US011525670B2

(12) United States Patent
Messerly et al.

(10) Patent No.: US 11,525,670 B2
(45) Date of Patent: Dec. 13, 2022

(54) SHAPE-SENSING SYSTEMS WITH FILTERS AND METHODS THEREOF

(71) Applicant: Bard Access Systems, Inc., Salt Lake City, UT (US)

(72) Inventors: Shayne Messerly, Kaysville, UT (US); Anthony K. Misener, Bountiful, UT (US); Chase Thompson, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 93 days.

(21) Appl. No.: 17/105,259

(22) Filed: Nov. 25, 2020

(65) Prior Publication Data

US 2021/0156676 A1    May 27, 2021

Related U.S. Application Data

(60) Provisional application No. 62/940,100, filed on Nov. 25, 2019.

(51) Int. Cl.
*G01B 11/24* (2006.01)
*G01B 11/16* (2006.01)

(52) U.S. Cl.
CPC ............ *G01B 11/24* (2013.01); *G01B 11/161* (2013.01); *G01B 11/165* (2013.01)

(58) Field of Classification Search
CPC ........ A61B 17/3403; A61B 2017/3413; A61B 2034/2051; A61B 2034/2063;
(Continued)

(56) References Cited

U.S. PATENT DOCUMENTS

| 4,813,429 A | 3/1989 | Eshel et al. |
| 5,099,845 A | 3/1992 | Besz et al. |

(Continued)

FOREIGN PATENT DOCUMENTS

| DE | 102016109601 A1 | 11/2017 |
| EP | 2240111 A2 | 10/2010 |

(Continued)

OTHER PUBLICATIONS

PCT/US2021/054802 filed Oct. 13, 2021 International Search Report and Written Opinion dated Feb. 2, 2022.
(Continued)

*Primary Examiner* — Tarifur R Chowdhury
*Assistant Examiner* — Roberto Fabian, Jr.
(74) *Attorney, Agent, or Firm* — Rutan & Tucker LLP

(57) ABSTRACT

Shape-sensing systems and methods for medical devices. The shape-sensing system can include a medical device, an optical interrogator, a console, and a display screen. The medical device can include an integrated optical-fiber stylet having fiber Bragg grating ("FBG") sensors along at least a distal-end portion thereof. The optical interrogator can be configured to send input optical signals into the optical-fiber stylet and receive FBG sensor-reflected optical signals therefrom. The console can be configured to convert the reflected optical signals with the aid of filtering algorithms of some optical signal-converter algorithms into plottable data for displaying plots thereof on the display screen. The plots can include a plot of curvature vs. time for each FBG sensor of a selection of the FBG sensors for identifying a distinctive change in strain of the optical-fiber stylet as a tip of the medical device is advanced into a superior vena cava of a patient.

24 Claims, 11 Drawing Sheets

(58) Field of Classification Search
CPC ... A61B 2090/378; A61B 34/20; A61B 34/25;
A61B 8/0841; A61B 8/461; A61B 8/467;
A61B 5/024; A61B 5/0084; A61B 5/065;
A61B 5/725; A61B 2034/2061
See application file for complete search history.

(56) References Cited

U.S. PATENT DOCUMENTS

| | | |
|---|---|---|
| 5,163,935 A | 11/1992 | Black et al. |
| 5,207,672 A | 5/1993 | Roth et al. |
| 5,211,165 A | 5/1993 | Dumoulin et al. |
| 5,275,151 A | 1/1994 | Shockey et al. |
| 5,423,321 A | 6/1995 | Fontenot |
| 5,454,807 A | 10/1995 | Lennox et al. |
| 5,517,997 A | 5/1996 | Fontenot |
| 5,622,170 A | 4/1997 | Schulz |
| 5,740,808 A | 4/1998 | Panescu et al. |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,360,630 B2 | 6/2016 | Jenner et al. |
| 9,560,954 B2 | 2/2017 | Jacobs et al. |
| 9,622,706 B2 | 4/2017 | Dick et al. |
| 9,678,275 B1 | 6/2017 | Griffin |
| 10,231,753 B2 | 3/2019 | Burnside et al. |
| 10,327,830 B2 | 6/2019 | Grant et al. |
| 10,349,890 B2 | 7/2019 | Misener et al. |
| 10,492,876 B2 | 12/2019 | Anastassiou et al. |
| 10,568,586 B2 | 2/2020 | Begin et al. |
| 10,631,718 B2 | 4/2020 | Petroff et al. |
| 10,992,078 B2 | 4/2021 | Thompson et al. |
| 11,123,047 B2 | 9/2021 | Jaffer et al. |
| 2002/0198457 A1 | 12/2002 | Tearney et al. |
| 2003/0092995 A1 | 5/2003 | Thompson |
| 2004/0242995 A1 | 12/2004 | Maschke |
| 2005/0033264 A1 | 2/2005 | Redinger |
| 2006/0013523 A1 | 1/2006 | Chiidlers et al. |
| 2006/0036164 A1 | 2/2006 | Wilson et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0156019 A1 | 7/2007 | Larkin et al. |
| 2007/0201793 A1 | 8/2007 | Askins et al. |
| 2007/0287886 A1 | 12/2007 | Saadat |
| 2007/0299425 A1 | 12/2007 | Waner et al. |
| 2008/0172119 A1 | 7/2008 | Yamasaki et al. |
| 2008/0183128 A1 | 7/2008 | Morriss et al. |
| 2008/0285909 A1 | 11/2008 | Younge et al. |
| 2009/0062634 A1 | 3/2009 | Say et al. |
| 2009/0137952 A1 | 5/2009 | Ramamurthy et al. |
| 2009/0234328 A1 | 9/2009 | Cox et al. |
| 2009/0304582 A1 | 12/2009 | Rousso et al. |
| 2010/0016729 A1 | 1/2010 | Futrell |
| 2010/0030063 A1 | 2/2010 | Lee et al. |
| 2010/0114115 A1 | 5/2010 | Schlesinger et al. |
| 2011/0144481 A1 | 6/2011 | Feer et al. |
| 2011/0166442 A1 | 7/2011 | Sarvazyan |
| 2011/0172680 A1 | 7/2011 | Younge et al. |
| 2011/0245662 A1 | 10/2011 | Eggers et al. |
| 2012/0046562 A1 | 2/2012 | Powers et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0188855 A1 | 7/2013 | Desjardins et al. |
| 2013/0204124 A1 | 8/2013 | Duindam et al. |
| 2013/0211246 A1 | 8/2013 | Parasher |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0121468 A1 | 5/2014 | Eichenholz |
| 2014/0221829 A1 | 8/2014 | Maitland et al. |
| 2014/0275997 A1 | 9/2014 | Chopra et al. |
| 2015/0029511 A1 | 1/2015 | Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0209113 A1 | 7/2015 | Burkholz et al. |
| 2015/0209117 A1* | 7/2015 | Flexman ............... A61B 34/20 |
| | | 600/424 |
| 2015/0320977 A1 | 11/2015 | Vitullo et al. |
| 2016/0018602 A1 | 1/2016 | Govari et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0354038 A1 | 12/2016 | Demirtas et al. |
| 2017/0020394 A1 | 1/2017 | Harrington |
| 2017/0079681 A1* | 3/2017 | Burnside ............... A61B 5/062 |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0311901 A1* | 11/2017 | Zhao ............... A61B 5/1102 |

(56) References Cited

U.S. PATENT DOCUMENTS

| | | | |
|---|---|---|---|
| 2017/0319279 | A1* | 11/2017 | Fish .................. A61B 18/1206 |
| 2018/0095231 | A1 | 4/2018 | Lowell et al. |
| 2018/0113038 | A1 | 4/2018 | Janabi-Sharifi et al. |
| 2018/0140170 | A1 | 5/2018 | Van Putten et al. |
| 2018/0239124 | A1 | 8/2018 | Naruse et al. |
| 2018/0250088 | A1 | 9/2018 | Brennan et al. |
| 2018/0264227 | A1 | 9/2018 | Flexman et al. |
| 2018/0289390 | A1 | 10/2018 | Amorizzo et al. |
| 2018/0289927 | A1 | 10/2018 | Messerly |
| 2018/0339134 | A1 | 11/2018 | Leo |
| 2018/0360545 | A1 | 12/2018 | Cole et al. |
| 2019/0059743 | A1 | 2/2019 | Ramachandran et al. |
| 2019/0110844 | A1 | 4/2019 | Misener et al. |
| 2019/0231272 | A1* | 8/2019 | Yamaji .................. A61B 5/0245 |
| 2019/0237902 | A1 | 8/2019 | Thompson et al. |
| 2019/0321110 | A1 | 10/2019 | Grunwald et al. |
| 2019/0343424 | A1 | 11/2019 | Blumenkranz et al. |
| 2019/0357875 | A1 | 11/2019 | Qi et al. |
| 2020/0046434 | A1 | 2/2020 | Graetzel et al. |
| 2020/0305983 | A1 | 10/2020 | Yampolsky et al. |
| 2021/0045814 | A1 | 2/2021 | Thompson et al. |
| 2021/0298680 | A1 | 3/2021 | Sowards et al. |
| 2021/0268229 | A1 | 9/2021 | Sowards et al. |
| 2021/0271035 | A1 | 9/2021 | Sowards et al. |
| 2021/0275257 | A1 | 9/2021 | Prior et al. |
| 2021/0401456 | A1 | 12/2021 | Cox et al. |
| 2021/0401509 | A1 | 12/2021 | Misener et al. |
| 2021/0402144 | A1 | 12/2021 | Messerly |
| 2022/0034733 | A1 | 2/2022 | Misener et al. |
| 2022/0110695 | A1 | 4/2022 | Sowards et al. |
| 2022/0152349 | A1 | 5/2022 | Sowards et al. |
| 2022/0160209 | A1 | 5/2022 | Sowards et al. |
| 2022/0211442 | A1 | 7/2022 | McLaughlin et al. |

FOREIGN PATENT DOCUMENTS

| | | | |
|---|---|---|---|
| EP | 3545849 | A1 | 10/2019 |
| WO | 99/64099 | A1 | 12/1999 |
| WO | 1999064099 | A1 | 12/1999 |
| WO | 2006122001 | A2 | 11/2006 |
| WO | 2009/155325 | A2 | 12/2009 |
| WO | 2011141830 | A1 | 11/2011 |
| WO | 2011150376 | A1 | 12/2011 |
| WO | 2012064769 | A2 | 5/2012 |
| WO | 2015074045 | A2 | 5/2015 |
| WO | 2016/061431 | A1 | 4/2016 |
| WO | 2018/096491 | A1 | 5/2018 |
| WO | 2019037071 | A1 | 2/2019 |
| WO | 2019/046769 | A1 | 3/2019 |
| WO | 2019230713 | A1 | 12/2019 |
| WO | 2021030092 | A1 | 2/2021 |
| WO | 2021108688 | A1 | 6/2021 |
| WO | 2021108697 | A1 | 6/2021 |
| WO | 2022/031613 | A1 | 2/2022 |
| WO | 2022/081723 | A1 | 4/2022 |

OTHER PUBLICATIONS

PCT/US2021/060849 filed Nov. 24, 2021 International Search Report and Written Opinion dated Mar. 9, 2022.
U.S. Appl. No. 15/947,267, filed Apr. 6, 2018 Final Office Action dated Apr. 22, 2022.
U.S. Appl. No. 17/185,777, filed Feb. 25, 2021 Non-Final Office Action dated Feb. 9, 2022.
PCT/US2021/020732 filed Mar. 3, 2021 International Search Report and Written Opinion dated Jul. 5, 2021.
PCT/US2020/062396 filed Nov. 25, 2020 International Search Report and Written Opinion dated Mar. 2, 2021.
PCT/US2020/062407 filed Nov. 25, 2020 International Search Report and Written Opinion dated Mar. 11, 2021.
PCT/US2018/026493 filed Apr. 6, 2018 International Search Report and Written Opinion dated Jun. 22, 2018.
PCT/US2020/044801 filed Aug. 3, 2020 International Search Report and Written Opinion dated Oct. 26, 2020.
PCT/US2021/019713 filed Feb. 25, 2021 International Search Report and Written Opinion dated Jul. 6, 2021.
PCT/US2021/020079 filed Feb. 26, 2021 International Search Report and Written Opinion dated Jun. 4, 2021.
U.S. Appl. No. 15/947,267, filed Apr. 6, 2018 Final Office Action dated Jun. 30, 2021.
U.S. Appl. No. 15/947,267, filed Apr. 6, 2018 Final Office Action dated Nov. 10, 2020.
U.S. Appl. No. 15/947,267, filed Apr. 6, 2018 Non-Final Office Action dated Mar. 12, 2021.
U.S. Appl. No. 15/947,267, filed Apr. 6, 2018 Non-Final Office Action dated May 29, 2020.
U.S. Appl. No. 15/947,267, filed Apr. 6, 2018 Non-Final Office Action dated Oct. 13, 2021.
PCT/US2021/038899 filed Jun. 24, 2021 International Search Report and Written Opinion dated Oct. 6, 2021.
PCT/US2021/038954 filed Jun. 24, 2021 International Search Report and Written Opinion dated Oct. 28, 2021.
PCT/US2021/041128 filed Jul. 9, 2021 International Search Report and Written Opinion dated Oct. 25, 2021.
PCT/US2021/044216 filed Aug. 2, 2021 International Search Report and Written Opinion dated Nov. 18, 2021.
PCT/US2020/062396 filed Nov. 25, 2020 International Preliminary Report on Patentability dated Jan. 29, 2021.
PCT/US2020/062407 filed Nov. 25, 2020 International Preliminary Report on Patentability dated Jan. 25, 2021.
PCT/US2022/011347 filed Jan. 5, 2022 International Search Report and Written Opinion dated May 3, 2022.
PCT/US2022/013897 filed Jan. 26, 2022 International Search Report and Written Opinion dated May 11, 2022.
U.S. Appl. No. 17/371,993, filed Jul. 9, 2021 Non-Final Office Action dated Jul. 12, 2022.

* cited by examiner

SHAPE-SENSING SYSTEMS WITH FILTERS AND METHODS THEREOF

PRIORITY

This application claims the benefit of priority to U.S. Provisional Application No. 62/940,100, filed Nov. 25, 2019, which is incorporated by reference in its entirety into this application.

BACKGROUND

At times, a tip of a peripherally inserted central catheter ("PICC") or central venous catheter ("CVC") can move becoming displaced from an ideal position in a patient's superior vena cava ("SVC"). A clinician believing such a PICC or CVC has displaced typically checks for displacement by chest X-ray and replaces the PICC or CVC if necessary. However, X-rays expose patients to ionizing radiation. Therefore, there is a need for clinicians to easily and safely check for displacement of PICCs and CVCs for replacement thereof if necessary.

Disclosed herein are shape-sensing systems with filters and methods thereof that address the foregoing.

SUMMARY

Disclosed herein is a shape-sensing system including, in some embodiments, one or more medical devices including an integrated optical-fiber stylet and a heartbeat-detecting means for detecting a sequence of heartbeats, a console, and a display screen. The optical-fiber stylet has a plurality of fiber Bragg grating ("FBG") sensors along a distal-end portion of the optical-fiber stylet. The console includes memory and one or more processors. The console is configured to convert the sequence of heartbeats into a heartbeat frequency by way of a heartbeat-converter algorithm. The console is configured to convert FBG sensor-reflected optical signals from the optical-fiber stylet into plottable data by way of a plurality of optical signal-converter algorithms. The optical signal-converter algorithms include a band-pass filtering algorithm for a selection of the FBG sensors along a distal-end portion of the optical-fiber stylet. The band-pass filtering algorithm is configured to pass therethrough the FBG sensor-reflected optical signals, or corresponding data, occurring with one or more frequencies within a range of frequencies around the heartbeat frequency while rejecting the FBG sensor-reflected optical signals, or the corresponding data, occurring with one or more frequencies outside the range of frequencies around the heartbeat frequency. The display screen is configured for displaying any plot of a plurality of plots of the plottable data. The plurality of plots include a plot of curvature vs. time for each FBG sensor of the selection of the FBG sensors for identifying periodic changes in strain of the optical-fiber stylet at a moment a tip of the optical-fiber stylet is advanced into a heart of a patient.

In some embodiments, the optical signal-converter algorithms include a band-stop filtering algorithm for the FBG sensors proximal of the selection of the FBG sensors. The band-stop filtering algorithm is configured to reject the FBG sensor-reflected optical signals, or the corresponding data, occurring with one or more frequencies within the range of frequencies around the heartbeat frequency while passing therethrough the FBG sensor-reflected optical signals, or the corresponding data, occurring with one or more frequencies outside the range of frequencies around the heartbeat frequency.

In some embodiments, the plurality of plots include a displayable shape over a 3-dimensional grid corresponding to the optical-fiber stylet in 3-dimensional space. The displayable shape is substantially free from heartbeat-related hydrodynamic noise.

In some embodiments, the heartbeat-detecting means is incorporated into a same medical device as that including the optical-fiber stylet.

In some embodiments, the same medical device including the optical-fiber stylet has electrocardiogram ("ECG") electrodes electrically connected by a cable to ECG componentry in the console for detecting the sequence of heartbeats.

In some embodiments, the same medical device includes the optical-fiber stylet having one or more lumens configured to contain a saline solution. The medical device includes a cable to connect the one-or-more lumens when filled with the saline solution to ECG componentry in the console for detecting the sequence of heartbeats.

In some embodiments, the heartbeat-detecting means is incorporated into a different medical device than that including the optical-fiber stylet.

In some embodiments, the different medical device includes ECG skin electrodes electrically connected to ECG componentry in the console for detecting the sequence of heartbeats.

In some embodiments, the console includes a heart-determiner algorithm configured to automatically confirm on the display the tip of the optical-fiber stylet is in the heart of the patient by way of the periodic changes in the strain of the optical-fiber stylet sensed by the selection of the FBG sensors. The periodic changes in the strain resulting from heartbeat-related hydrodynamics.

In some embodiments, the shape-sensing system further includes an optical interrogator configured to send input optical signals into the optical-fiber stylet and receive the FBG sensor-reflected optical signals from the optical-fiber stylet. The optical interrogator is either a stand-alone optical interrogator or an integrated optical interrogator integrated into the console.

Also disclosed herein is a method of a shape-sensing system including, in some embodiments, a shape-sensing step of shape sensing with an optical-fiber stylet of the shape-sensing system while a tip of the optical-fiber stylet is advanced through a vasculature of a patient toward a heart. The optical-fiber stylet has a plurality of FBG sensors along a distal-end portion of the optical-fiber stylet for the shape sensing. The method further includes a detecting step of detecting a sequence of heartbeats with a heartbeat-detecting means of the shape-sensing system for detecting the sequence of heartbeats while the tip of the optical-fiber stylet is advanced through the vasculature of the patient toward the heart. The method further includes a first converting step of converting the sequence of heartbeats into a heartbeat frequency by way of a heartbeat-converter algorithm of a console of the shape-sensing system.

The method further includes a second converting step of converting FBG sensor-reflected optical signals received from the optical-fiber stylet into plottable data by way of a plurality of optical signal-converter algorithms of the console. The second converting step includes passing the FBG sensor-reflected optical signals, or corresponding data, for a selection of the FBG sensors along a distal-end portion of the optical-fiber stylet through a band-pass filtering algorithm of the optical signal-converter algorithms. The band-pass filtering algorithm is configured to pass therethrough the FBG sensor-reflected optical signals, or the corresponding data, for the selection of the FBG sensors occurring with one or more frequencies within a range of frequencies around the heartbeat frequency while rejecting the FBG sensor-reflected optical signals, or the corresponding data, occurring with one or more frequencies outside the range of frequencies around the heartbeat frequency. The method further includes a plotting step of plotting a plurality of plots including a plot of curvature vs. time for each FBG sensor of the selection of the FBG sensors on a display screen of the shape-sensing system. The method further includes a displaying step of displaying on the display screen periodic changes in strain in the plot of curvature vs. time for any FBG sensor of the selection of the FBG sensors at a moment the tip of the optical-fiber stylet is advanced into the heart of the patient.

In some embodiments, the second converting step includes passing the FBG sensor-reflected optical signals, or the corresponding data, for the FBG sensors proximal of the selection of the FBG sensors through a band-stop filtering algorithm of the optical signal-converter algorithms. The band-stop filtering algorithm is configured to reject the FBG sensor-reflected optical signals, or the corresponding data, occurring with one or more frequencies within the range of frequencies around the heartbeat frequency while passing therethrough the FBG sensor-reflected optical signals, or the corresponding data, occurring with one or more frequencies outside the range of frequencies around the heartbeat frequency.

In some embodiments, the plurality of plots includes a displayable shape over a 3-dimensional grid corresponding to the optical-fiber stylet in 3-dimensional space. The displayable shape is substantially free from heartbeat-related hydrodynamic noise.

In some embodiments, the heartbeat-detecting means includes ECG electrodes of a medical device including the optical-fiber stylet, ECG skin electrodes, or a combination thereof connected to ECG componentry in the console for detecting the sequence of heartbeats.

In some embodiments, the method further includes a signal-sending step of sending input optical signals into the optical-fiber stylet by an optical interrogator and a signal-receiving step of receiving the FBG sensor-reflected optical signals from the optical-fiber stylet with the optical interrogator. The optical interrogator being either a stand-alone optical interrogator or an integrated optical interrogator integrated into the console.

Also disclosed herein is a method for determining a tip of a medical device is located within a heart including, in some embodiments, an advancing step of advancing the tip of the medical device through a vasculature of a patient toward the heart. The medical device includes an integrated optical-fiber stylet having a plurality of FBG sensors along a distal-end portion of the optical-fiber stylet for shape sensing with a shape-sensing system including the medical device. The method further includes a detecting step of detecting a sequence of heartbeats with a heartbeat-detecting means of the shape-sensing system for detecting the sequence of heartbeats while advancing the tip of the medical device through the vasculature of the patient toward the heart. The method further includes a first allowing step of allowing the sequence of heartbeats to be converted into a heartbeat frequency by way of a heartbeat-converter algorithm of a console of the shape-sensing system.

The method further includes a second allowing step of allowing FBG sensor-reflected optical signals received from the optical-fiber stylet while advancing the tip of the medical device through the vasculature of the patient to be converted into plottable data by way of a plurality of optical signal-converter algorithms of the console. The optical signal-converter algorithms include a band-pass filtering algorithm for a selection of the FBG sensors along a distal-end portion of the optical-fiber stylet. The band-pass filtering algorithm is configured to pass therethrough the FBG sensor-reflected optical signals or corresponding data occurring with one or more frequencies within a range of frequencies around the heartbeat frequency while rejecting the FBG sensor-reflected optical signals or corresponding data occurring with one or more frequencies outside the range of frequencies around the heartbeat frequency. The method further includes a third allowing step of allowing a plurality of plots including a plot of curvature vs. time for each FBG sensor of the selection of the FBG sensors to be plotted on a display screen of the shape-sensing system. The method further includes an identifying step of identifying on the display screen periodic changes in strain in the plot of curvature vs. time for any FBG sensor of the selection of the FBG sensors at a moment the tip of the medical device is advanced into the heart of the patient, thereby determining the tip of the medical device is located within the heart.

In some embodiments, the optical signal-converter algorithms include a band-stop filtering algorithm for the FBG sensors proximal of the selection of the FBG sensors. The band-stop filtering algorithm is configured to reject the FBG sensor-reflected optical signals, or corresponding data, occurring with one or more frequencies within the range of frequencies around the heartbeat frequency while passing therethrough the FBG sensor-reflected optical signals, or the corresponding data, occurring with one or more frequencies outside the range of frequencies around the heartbeat frequency.

In some embodiments, the plurality of plots include a displayable shape over a 3-dimensional grid corresponding to the optical-fiber stylet in 3-dimensional space. The displayable shape is substantially free from heartbeat-related hydrodynamic noise.

In some embodiments, the heartbeat-detecting means includes ECG electrodes of the medical device, ECG skin electrodes, or a combination thereof connected to ECG componentry in the console for detecting the sequence of heartbeats.

In some embodiments, the advancing step includes advancing the tip of the medical device through a right internal jugular vein, a right brachiocephalic vein, and into an SVC.

In some embodiments, the optical-fiber stylet is disposed in a central venous catheter ("CVC").

In some embodiments, the advancing step includes advancing the tip of the medical device through a right basilic vein, a right axillary vein, a right subclavian vein, a right brachiocephalic vein, and into an SVC.

In some embodiments, the medical device is a peripherally inserted central catheter ("PICC").

In some embodiments, the method further includes a ceasing step of ceasing to advance the tip of the medical device through the vasculature of the patient after determining the tip of the medical device is located in the heart.

These and other features of the concepts provided herein will become more apparent to those of skill in the art in view of the accompanying drawings and following description, which describe particular embodiments of such concepts in greater detail.

DRAWINGS

Figure 10:
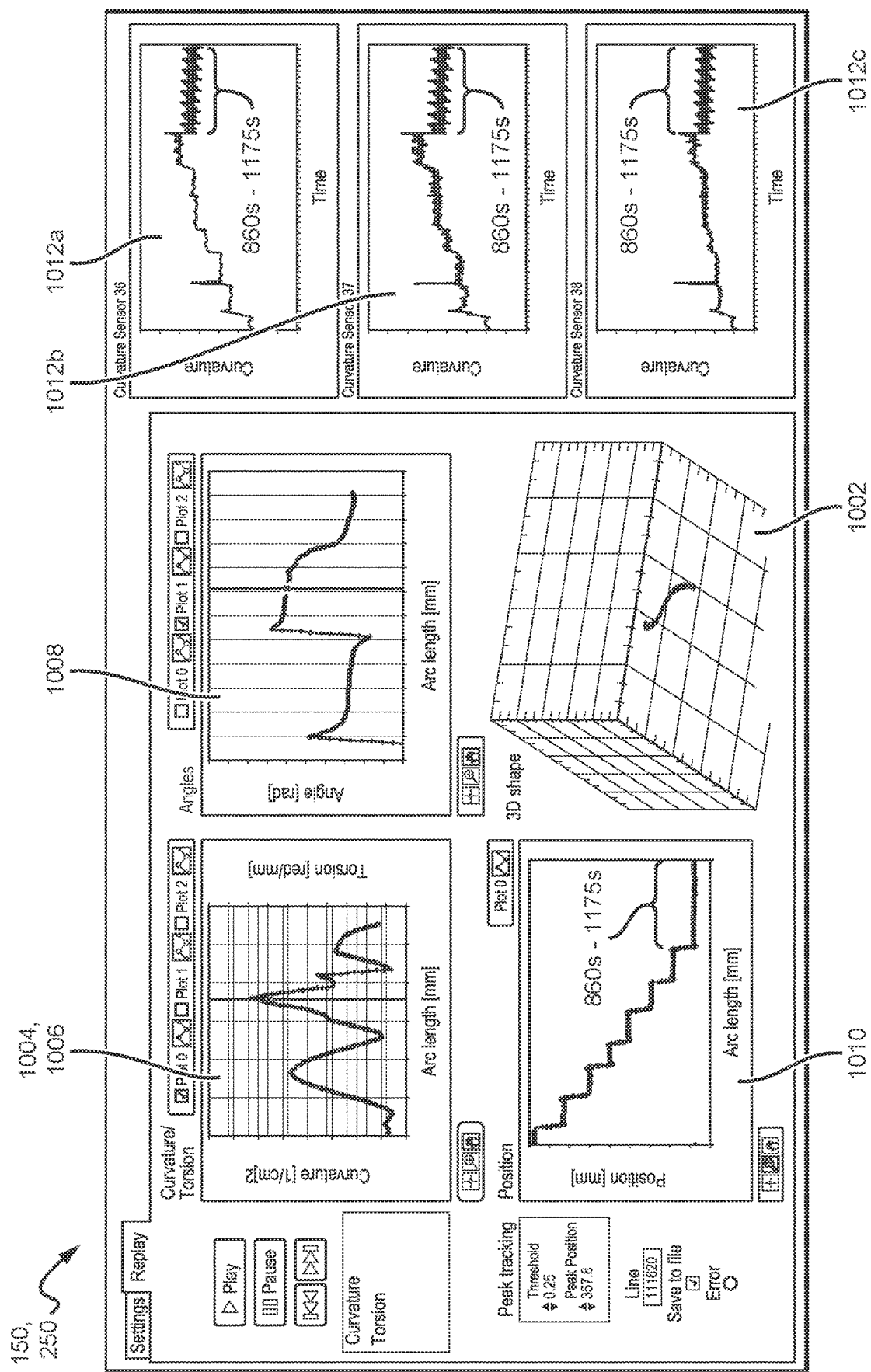

FIG. 10 provides a number of different plots on a display screen of a shape-sensing system in accordance with some embodiments.

Figure 11:
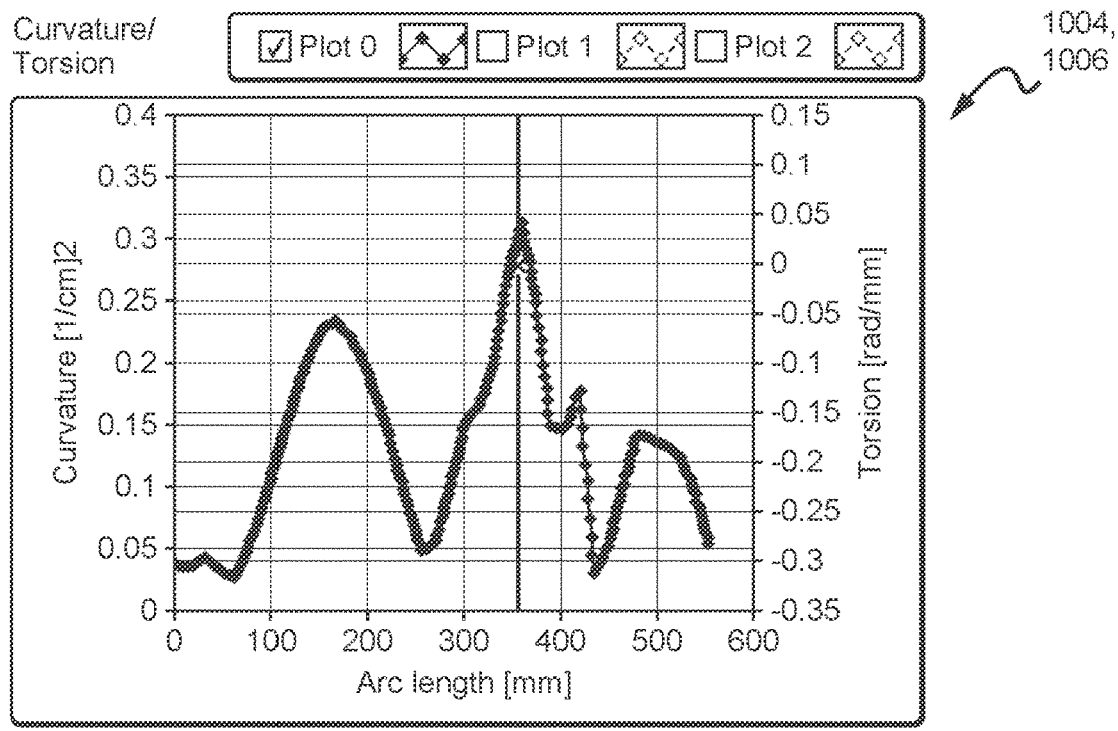

FIG. 11 provides a detailed plot of curvature vs. arc length and torsion vs. arc length for at least a distal-end portion of an optical-fiber stylet as one of the plots of FIG. 10.

Figure 12:
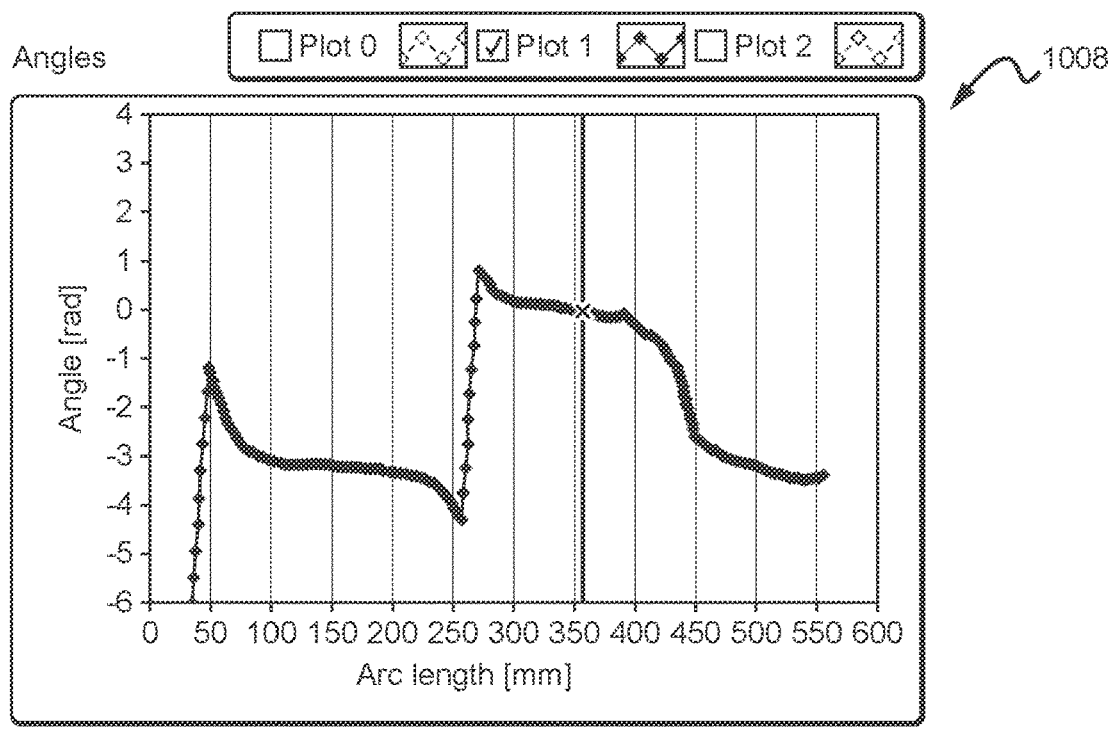

FIG. 12 provides a detailed plot of angle vs. arc length for at least a distal-end portion of an optical-fiber stylet as one of the plots of FIG. 10.

Figure 13:
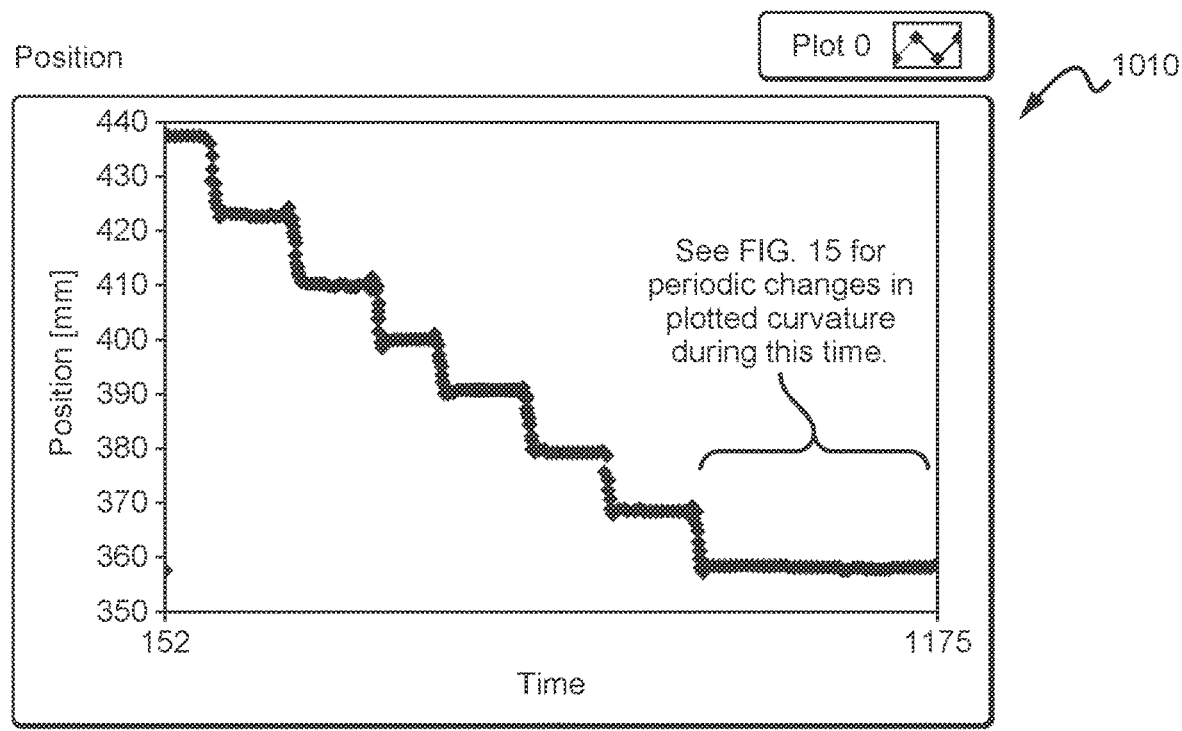

FIG. 13 provides a detailed plot of position vs. time for at least a distal-end portion of an optical-fiber stylet as one of the plots of FIG. 10.

Figure 14:
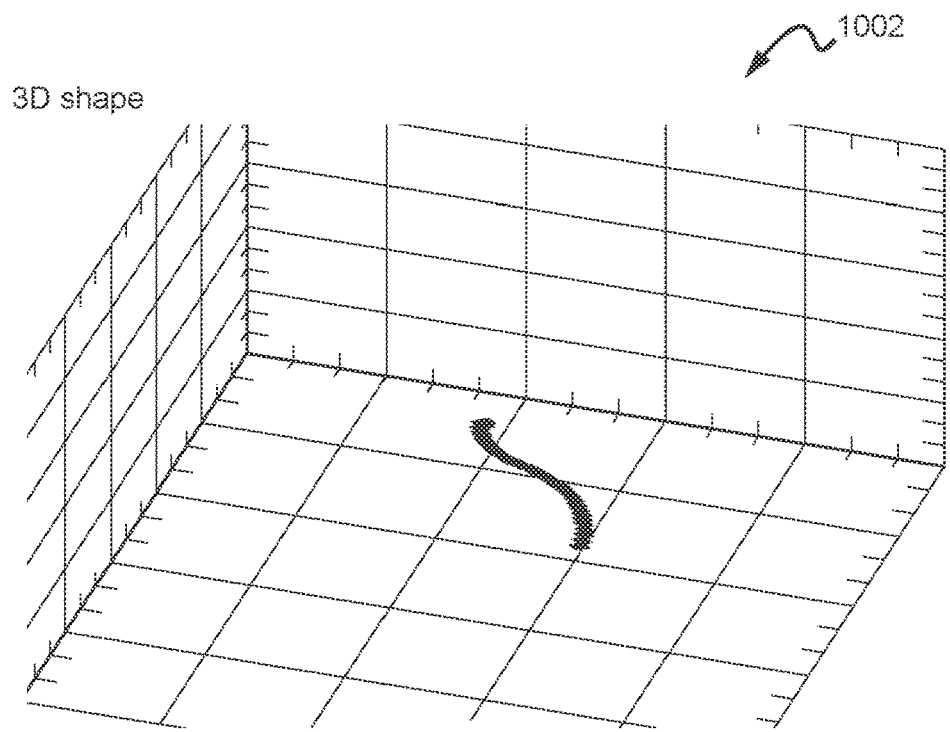

FIG. 14 provides a displayable shape for at least a distal-end portion of a medical device or an optical-fiber stylet in accordance with some embodiments.

Figure 15:
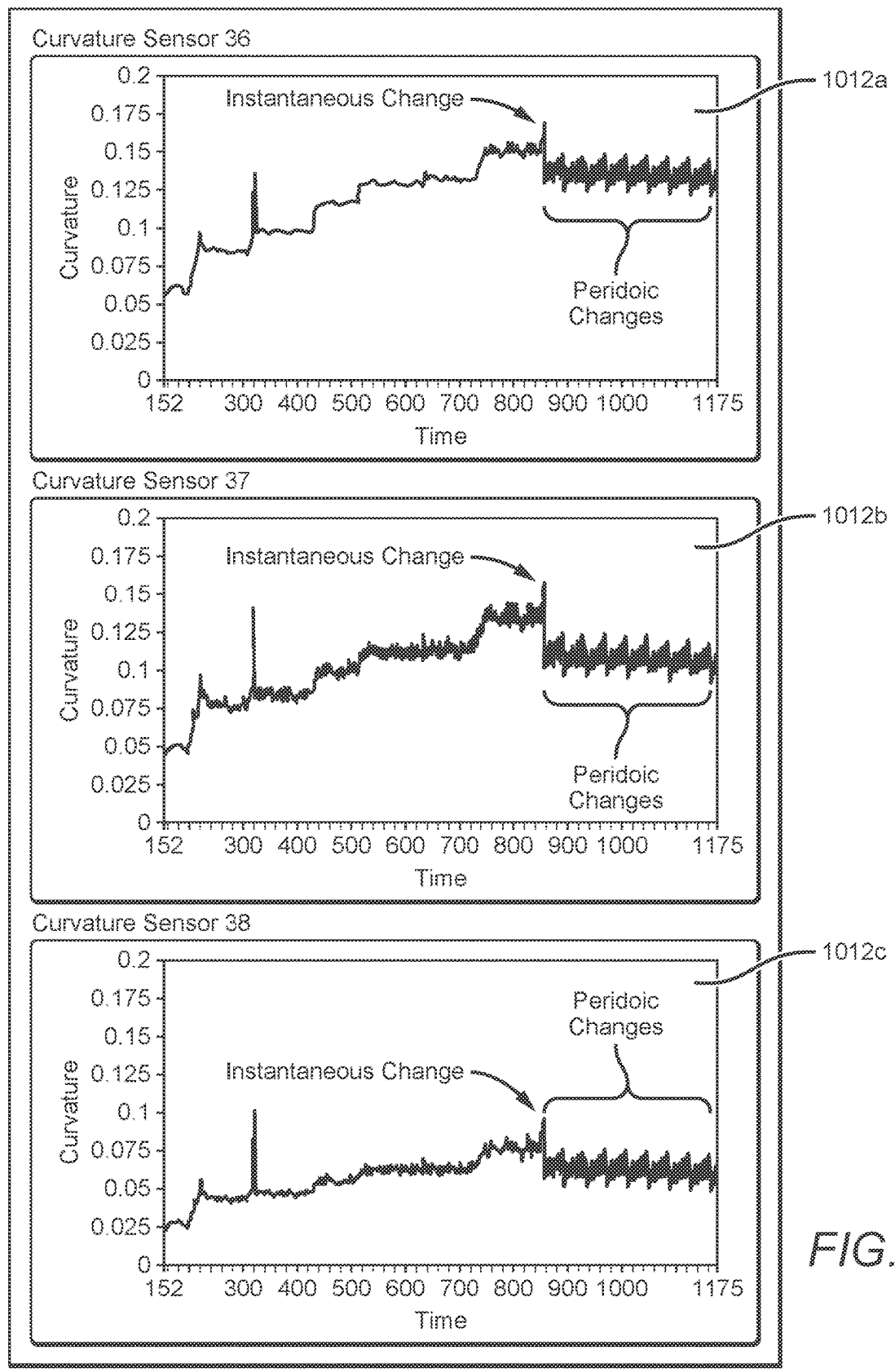

FIG. 15 provides detailed plots of curvature vs. time for each FBG sensor selected from a number of FBG sensors of an optical-fiber stylet as some of the plots of FIG. 10.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need for clinicians to easily and safely check for displacement of PICCs and CVCs for replacement thereof if necessary. Disclosed herein are shape-sensing systems with filters and methods thereof that address the foregoing.

For example, a shape-sensing system includes, in some embodiments, one or more medical devices including an integrated optical-fiber stylet and a heartbeat-detecting means for detecting a sequence of heartbeats, a console, and a display screen. The optical-fiber stylet has a number of FBG sensors along a distal-end portion of the optical-fiber stylet. The console includes memory and one or more processors. The console is configured to convert the sequence of heartbeats into a heartbeat frequency by way of a heartbeat-converter algorithm. The console is configured to convert FBG sensor-reflected optical signals from the optical-fiber stylet into plottable data by way of a number of optical signal-converter algorithms. The optical signal-converter algorithms include a band-pass filtering algorithm for a selection of the FBG sensors along a distal-end portion of the optical-fiber stylet. The band-pass filtering algorithm is configured to pass therethrough the FBG sensor-reflected optical signals, or corresponding data, occurring with one or more frequencies within a range of frequencies around the heartbeat frequency while rejecting the FBG sensor-reflected optical signals, or the corresponding data, occurring with one or more frequencies outside the range of frequencies around the heartbeat frequency. The display screen is configured for displaying any plot of a number of plots of the plottable data. The number of plots include a plot of curvature vs. time for each FBG sensor of the selection of the FBG sensors for identifying periodic changes in strain of the optical-fiber stylet at a moment a tip of the optical-fiber stylet is advanced into a heart of a patient.

These and other features of the shape-sensing systems with filters and methods provided herein will become more apparent with reference to the accompanying drawings and the following description, which provide particular embodiments of the shape-sensing systems with filters and methods thereof in greater detail.

Shape-Sensing Systems

Figure 2:
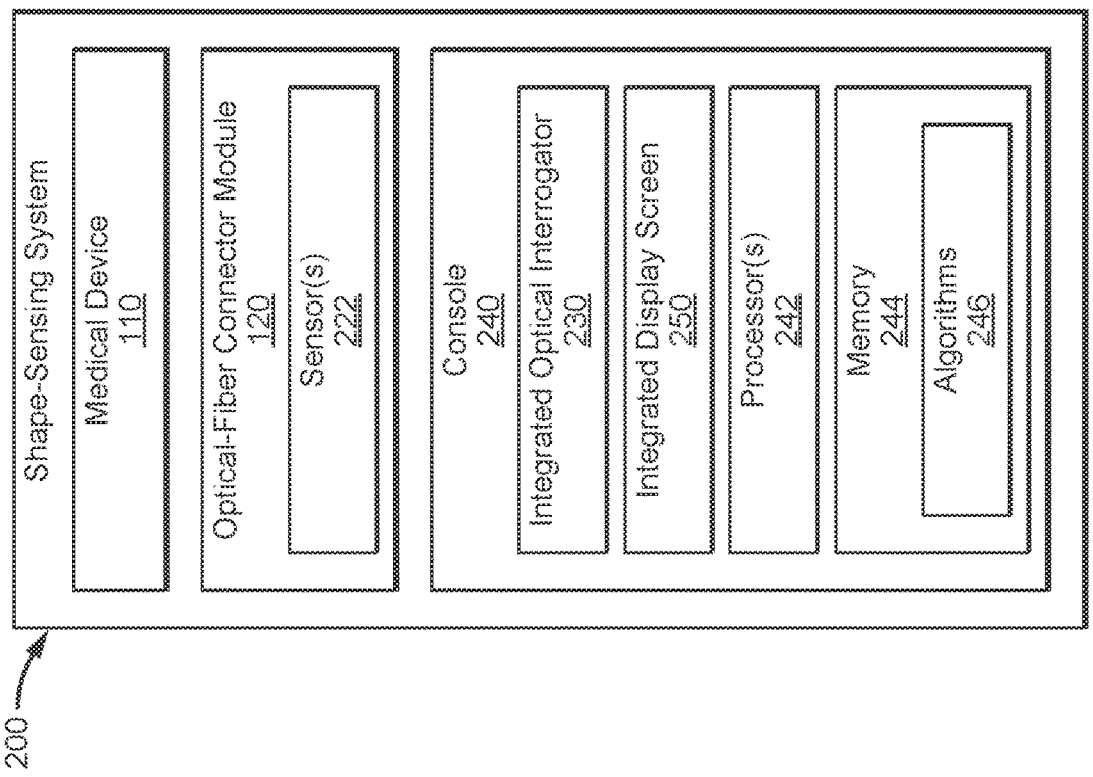
FIG. 2 is a block diagram of a second shape-sensing system in accordance with some embodiments.
Figure 1:
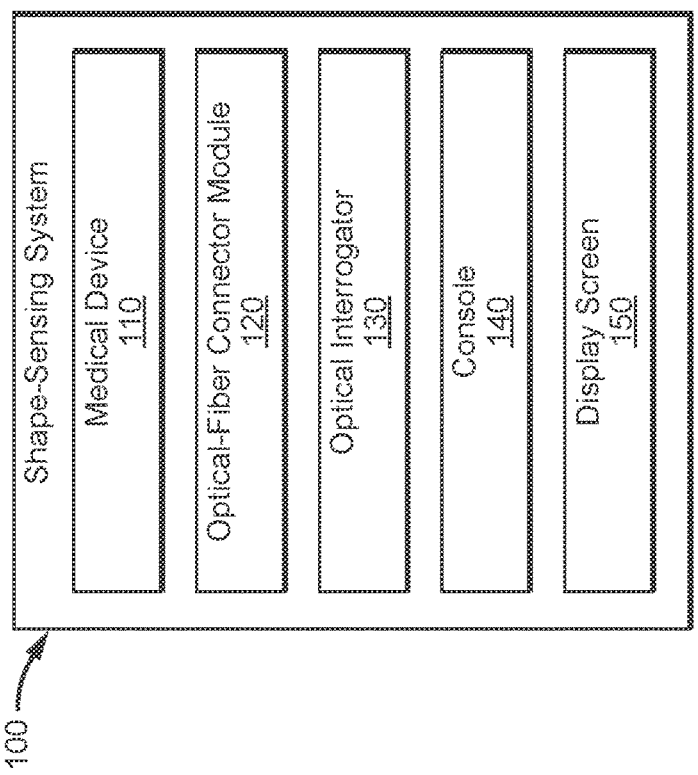
FIG. 1 is a block diagram of a first shape-sensing system in accordance with some embodiments.
Figure 3:
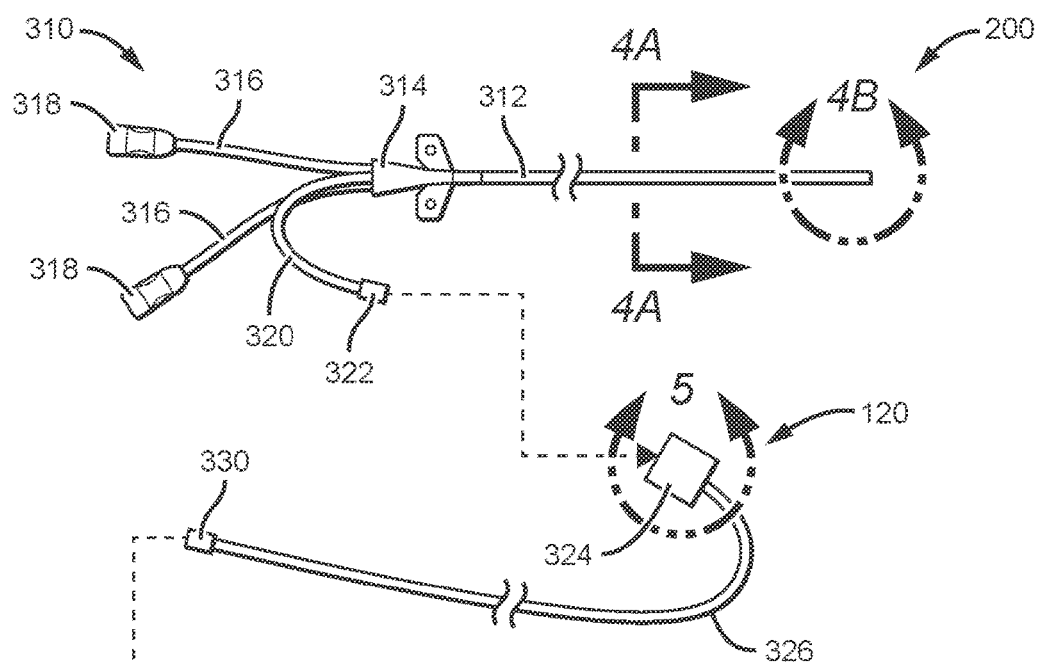
FIG. 3 illustrates the second shape-sensing system in accordance with some embodiments.
Figure 3:
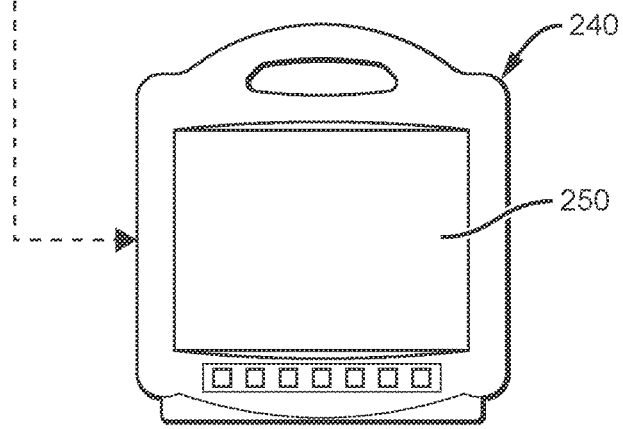

FIG. 1 is a block diagram of a first shape-sensing system 100 in accordance with some embodiments. FIG. 2 is a block diagram of a second shape-sensing system 200 in accordance with some embodiments. FIG. 3 illustrates the second shape-sensing system 200 in accordance with some embodiments. FIG. 10 provides a display screen 150 or 250 of the shape-sensing system 100 or 200 in accordance with some embodiments. FIGS. 11-15 provide detailed plots of a number of different plots on the display screen 150 or 250 of FIG. 10.

As shown, the shape-sensing system 100 includes at least a medical device 110, a stand-alone optical interrogator 130, a console 140, and the display screen 150 such as that of a stand-alone monitor. The shape-sensing system 200 includes the medical device 110, an integrated optical interrogator 230, a console 240, and the display screen 250, wherein both the integrated optical interrogator 230 and the display screen 250 are integrated into the console 240. Each shape-sensing system of the shape-sensing systems 100 and 200 can further include an optical-fiber connector module 120 configured for connecting the medical device 110 to a remainder of the shape-sensing system 100 or 200 such as the optical interrogator 130 or the console 240, which includes the integrated optical interrogator 230.

As set forth in more detail below, the medical device 110 includes an integrated optical-fiber stylet having a number of FBG sensors along at least a distal-end portion of the optical-fiber stylet for shape sensing with the shape-sensing system 100 or 200. (See the optical-fiber stylet 424 in FIG. 4B for an example of the optical-fiber stylet of the medical device 110.) The medical device 110 or a different medical device of the shape-sensing system 100 or 200 can include a heartbeat-detecting means for detecting a sequence of heartbeats.

Certain features of the medical device 110 are set forth in more detail below with respect to particular embodiments of the medical device 110 such as the PICC 310. That said, some features set forth below with respect to one or more embodiments of the medical device 110 are shared among two or more embodiments of the medical device 110. As such, "the medical device 110" is used herein to generically refer to more than one embodiment of the medical device 110 when needed for expository expediency. This is despite certain features having been described with respect to particular embodiments of the medical device 110 such as the PICC 310.

While only shown for the console 240, each console of the consoles 140 and 240 includes one or more processors 242 and memory 244 including a number of algorithms 246 such as one or more optical signal-converter algorithms including a band-pass filtering algorithm or a band-stop filtering algorithm, as well as a heartbeat-converter algorithm. The one-or-more optical signal-convertor algorithms are configured to convert the reflected optical signals from the optical-fiber stylet of the medical device 110 into plottable data for a number of plots of the plottable data. The one-or-more optical signal-converter algorithms are also configured to convert FBG sensor-reflected optical signals from the optical-fiber stylet of the medical device 110 into plottable data for a displayable shape corresponding to the medical device 110. The display screen 150 or 250 is configured to display the displayable shape for the medical device 110 over a 3-dimensional grid 1002 representing 3-dimensional space, as well as any plot of the number of plots of the other plottable data.

The number of plots can include a plot of curvature vs. arc length 1004, a plot of torsion vs. arc length 1006, a plot of angle vs. arc length 1008, or a plot of position vs. time 1010 for at least a distal-end portion of the optical-fiber stylet. The number of plots can further include at least a plot of curvature vs. time 1012a, 1012b, 1012c, . . . , 1012n, for each FBG sensor of a selection of the FBG sensors in the distal-end portion of the optical-fiber stylet. Any one or more of the plots of curvature vs. time 1012a, 1012b, 1012c, . . . , 1012n, for the selection of the FBG sensors in the distal-end portion of the optical-fiber stylet can be used to manually identify a distinctive change in strain of the optical-fiber stylet by way of a distinctive change in plotted curvature of the optical-fiber stylet at a moment a tip of the medical device 110 is advanced into a heat of a patient. However, the three plots of curvature vs. time 1012a, 1012b, and 1012c shown in FIGS. 10 and 15 are those for a last three FBG sensors in the distal-end portion of the optical-fiber stylet. The last three FBG sensors in the distal-end portion of the optical-fiber stylet are particularly useful in identifying the distinctive change in the plotted curvature of the optical-fiber stylet in that the foregoing FBG sensors directly experience a physical change in curvature resulting from tensile strain and compressive strain of the optical-fiber stylet when the tip of the medical device 110 is advanced into the heart of the patient. The distinctive change in the plotted curvature of the optical-fiber stylet is exemplified by an instantaneous increase in the plotted curvature followed by an instantaneous decrease in the plotted curvature having a magnitude about twice that of the instantaneous increase in the plotted curvature as shown by the arrow in any plot 1012a, 1012b, or 1012c of curvature vs. time shown in FIG. 15.

In addition to being able to use any one or more of the plots of curvature vs. time to manually identify the distinctive change in the strain of the optical-fiber stylet at the moment the tip of the medical device 110 is advanced into the heart of the patient, any one or more of the plots of curvature vs. time 1012a, 1012b, 1012c, . . . , 1012n, for the selection of the FBG sensors in the distal-end portion of the optical-fiber stylet can be used to manually confirm the tip of the medical device 110 is in the heart by way of periodic changes in the strain of the optical-fiber stylet. The periodic changes in the strain of the optical-fiber stylet are evidenced by periodic changes in the plotted curvature of the optical-fiber stylet sensed by the selection of the FBG sensors. (See the three plots of curvature vs. time 1012a, 1012b, and 1012c in FIGS. 10 and 15, between about 860 s and 1175 s when the distal-end portion of the optical-fiber stylet is held in position in the heart as shown by the plot of position vs. time 1010.) The periodic changes in the plotted curvature result from periodic changes in blood flow within the heart sensed by the selection of the FBG sensors as the heart of the patient beats.

The periodic changes in the strain sensed by any FBG sensor of the selection of the FBG sensors in the distal-end portion of the optical-fiber stylet are relatively small changes. Consequently, the periodic changes in the plotted curvature for any FBG sensor of the selection of the FBG sensors are also relatively small changes. Because such relatively small changes can be easily overwhelmed, it can be helpful to enhance the periodic changes in the plotted curvatures for the selection of the FBG sensors by filtering out strain experienced by the selection of the FBG sensors other than that resulting from the periodic changes periodic changes in blood flow within the heart.

As set forth above, the one-or-more optical signal-converter algorithms of the number of algorithms 246 includes a band-pass filtering algorithm, which is configured to facilitate identifying the periodic changes in the strain sensed by the optical-fiber stylet, particularly the strain sensed by any FBG sensor of the selection of the FBG sensors at a moment the tip of the optical-fiber stylet is advanced into a heart of a patient. The one-or-more optical signal-converter algorithms of the number of algorithms 246 also includes a band-stop filtering algorithm, which is configured to support displaying the displayable shape corresponding to the medical device 110 over the 3-dimensional grid 1002 representing 3-dimensional space. Indeed, the band-stop filtering algorithm is configured to support displaying the displayable shape such that the displayable shape is substantially free from heartbeat-related hydrodynamics or noise thereof. Each algorithm of the band-pass filtering algorithm and the band-stop filtering algorithm depend in part upon heartbeat frequency, which can be obtained from a patient by way the heartbeat-detecting means for detecting a sequence of heartbeats and the heartbeat converter algorithm for converting the sequence of heartbeats into the heartbeat frequency.

The heartbeat-detecting means can be incorporated into a same medical device as that including the optical-fiber stylet, namely the medical device 110, or a different medical device than that including the optical-fiber stylet. With respect to the same medical device as that including the optical-fiber stylet, the heartbeat-detecting means can include an ECG stylet disposed in the medical device 110 or ECG electrodes of the medical device 110 electrically connected by a cable to ECG componentry in the console 140 or 240 for detecting the sequence of heartbeats. Alternatively, the heartbeat-detecting means can include one or more lumens of the medical device 110 configured to contain a saline solution in accordance with the so-called saline technique, wherein a column of saline solution contained in a catheter is used as an intracavitary electrode. In such embodiments, the medical device 110 can include a cable to connect the one-or-more lumens when filled with the saline solution to the ECG componentry in the console 140 or 240 for detecting the sequence of heartbeats. With respect to the different medical device than that including the optical-fiber stylet, the heartbeat-detecting means can include ECG skin electrodes electrically connected to the ECG componentry in the console 140 or 240 for detecting the sequence of heartbeats.

The console 140 or 240 is configured to convert the sequence of heartbeats detected by the heartbeat detecting means into an instant heartbeat frequency by way of the heartbeat-converter algorithm of the number of algorithms 246, which heartbeat frequency, in turn, can be used by the band-pass filtering algorithm, the band-stop filtering algorithm, or both. The sequence of heartbeats can be constant over time with respect to diastolic or systolic points in the sequence of heartbeats, increasing over time with respect to the diastolic or systolic points in the sequence of heartbeats, decreasing over time with respect to the diastolic or systolic points in the sequence of heartbeats, or some combination thereof. Like the sequence of heartbeats from which the heartbeat frequency is derived, the heartbeat frequency can be constant, increase over time, decrease over time, or some combination thereof.

The console 140 or 240 is configured to convert the reflected optical signals from the optical-fiber stylet of the medical device 110 into the plottable data by way of the band-pass filtering algorithm of the one-or-more optical signal-convertor algorithms using the instant heartbeat frequency provided by the heartbeat-converter algorithm. The band-pass filtering algorithm is configured to pass therethrough the FBG sensor-reflected optical signals, or corresponding data, occurring with one or more frequencies within a range of frequencies around the heartbeat frequency while rejecting the FBG sensor-reflected optical signals, or the corresponding data, occurring with one or more frequencies outside the range of frequencies around the heartbeat frequency. Filtering the FBG sensor-reflected optical signals, or the corresponding data, with the band-pass filtering algorithm facilitates identifying the periodic changes in the strain sensed by the optical-fiber stylet, particularly the strain sensed by any FBG sensor of the selection of the FBG sensors, at a moment the tip of the medical device 110 or the optical-fiber stylet thereof is advanced into a heart of a patient. As set forth above, because such relatively small changes can be easily overwhelmed, it can be helpful to enhance the periodic changes in the plotted curvatures for the selection of the FBG sensors by filtering out strain experienced by the selection of the FBG sensors other than that resulting from the periodic changes in strain.

The console 140 or 240 is also configured to convert the reflected optical signals from the optical-fiber stylet of the medical device 110 into the plottable data by way of the band-stop filtering algorithm of the one-or-more optical signal-convertor algorithms using the instant heartbeat frequency provided by the heartbeat-converter algorithm. The band-stop filtering algorithm is configured to reject the FBG sensor-reflected optical signals, or corresponding data, occurring with one or more frequencies within the range of frequencies around the heartbeat frequency while passing therethrough the FBG sensor-reflected optical signals, or the corresponding data, occurring with one or more frequencies outside the range of frequencies around the heartbeat frequency. Filtering the FBG sensor-reflected optical signals, or the corresponding data, with the band-stop filtering algorithm supports displaying the displayable shape corresponding to the medical device 110 over the 3-dimensional grid 1002 representing 3-dimensional space, particularly a portion of the medical device 110 or the optical-fiber stylet thereof having the FBG sensors proximal of the selection of the FBG sensors. Indeed, the band-stop filtering algorithm is configured to support displaying the displayable shape such that the displayable shape is substantially free from heartbeat-related hydrodynamics or noise thereof.

In some embodiments, the band-pass filtering algorithm is configured to filter the FBG sensor-reflected optical signals, or the corresponding data, for the selection of the FBG sensors (e.g., a last three FBG sensors) in the distal-end portion of the optical-fiber stylet while the band-stop filtering algorithm is configured to filter the FBG sensor-reflected optical signals, or the corresponding data, for the FBG sensors proximal of the foregoing selection of the FBG sensors. In this way, the band-pass filtering algorithm facilitates identifying the periodic changes in the strain sensed by any FBG sensor of the selection of the FBG sensors in the distal-end portion of the optical-fiber stylet while the band-stop filtering algorithm supports displaying the displayable shape corresponding to a remainder of the medical device 110 proximal of the selection of the FBG sensors.

Each console of the consoles 140 and 240 can further include a heart-determiner algorithm of the one-or-more algorithms 246 configured to automatically determine the distinctive change in the strain of the optical-fiber stylet by way of a distinctive change in plotted curvature of the optical-fiber stylet, or the plottable data therefor, at the moment the tip of the medical device 110 is advanced into the heart of the patient. Again, the distinctive change in the plotted curvature is an instantaneous increase in the plotted curvature followed by an instantaneous decrease in the plotted curvature having a magnitude about twice that of the instantaneous increase in the plotted curvature. The heart-determiner algorithm can also be configured to confirm the tip of the medical device 110 is in the heart by way of automatically determining periodic changes in the plotted curvature of the optical-fiber stylet sensed by the selection of the FBG sensors. (See the three plots of curvature vs. time 1012a, 1012b, and 1012c in FIGS. 10 and 15, between about 860 s and 1175 s when the distal-end portion of the optical-fiber stylet is held in position in the heart as shown by the plot of position vs. time 1010.) The periodic changes in the plotted curvature result from heartbeat-related hydrodynamics or periodic changes in blood flow within the heart sensed by the selection of the FBG sensors as the heart of the patient beats.

The optical interrogator 130 or 230 is configured to send input optical signals into the optical-fiber stylet of the medical device 110 and receive the reflected optical signals from the optical-fiber stylet. When the optical-fiber connector module 120 is present in the shape-sensing system 100 or 200, the optical interrogator 130 or 230 is configured to send the input optical signals into the optical-fiber stylet of the medical device 110 by way of the optical-fiber connector module 120 and receive the reflected optical signals from the optical-fiber stylet by way of the optical-fiber connector module 120.

The optical-fiber connector module 120 includes a housing 324, a cable 326 extending from the housing 324, and an optical fiber 528 within at least the cable 326. (For the optical fiber 528, see FIG. 5.) The optical-fiber connector module 120 is configured to establish a first optical connection between the optical-fiber stylet of the medical device 110 and the optical fiber 528 of the optical-fiber connector module 120. The optical-fiber connector module 120 is also configured with a plug 330 at a terminus of the cable 326 to establish a second optical connection between the optical fiber 528 of the optical-fiber connector module 120 and the optical interrogator 130 or 230. The optical fiber 528 of the optical-fiber connector module 120 is configured to convey the input optical signals from the optical interrogator 130 or 230 to the optical-fiber stylet of the medical device 110 and the reflected optical signals from the optical-fiber stylet to the optical interrogator 130 or 230.

The optical-fiber connector module 120 can further include one or more sensors 222 selected from at least a gyroscope, an accelerometer, and a magnetometer disposed within the housing 324. The one-or-more sensors 222 are configured to provide sensor data to the console 140 or 240 by way of one or more data wires within at least the cable 326 for determining a reference plane with a reference plane-determiner algorithm of the one-or-more algorithms 246 for shape sensing with the optical-fiber stylet of the medical device 110.

Certain features of the optical-fiber connector module 120 are set forth in more detail below with respect to particular embodiments of the optical-fiber connector module 120 such as the optical-fiber connector module 620 and 820. That said, some features set forth below with respect to one or more embodiments of the optical-fiber connector module 120 are shared among two or more embodiments of the optical-fiber connector module 120. As such, "the optical-fiber connector module 120" is used herein to generically refer to more than one embodiment of the optical-fiber connector module 120 when needed for expository expediency. This is despite certain features having been described with respect to particular embodiments of the optical-fiber connector module 120 such as the optical-fiber connector modules 620 and 820.

Medical Devices

Figure 4A:
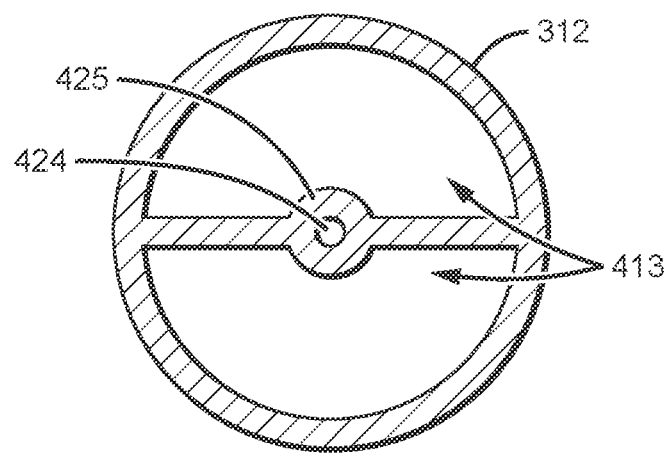
FIG. 4A illustrates a transverse cross-section of a catheter tube of a medical device in accordance with some embodiments.
Figure 4B:
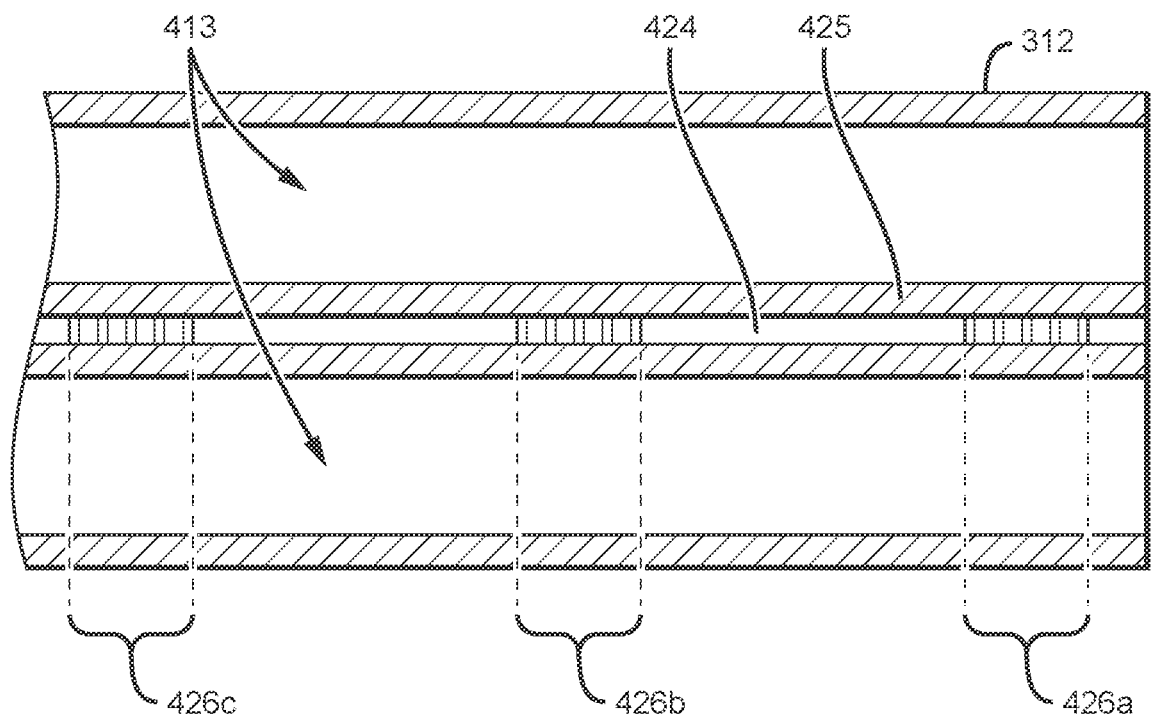
FIG. 4B illustrates a longitudinal cross-section of the catheter tube of the medical device in accordance with some embodiments.

FIG. 3 also illustrates a PICC 310 as the medical device 110 in accordance with some embodiments. FIG. 4A illustrates a transverse cross-section of a catheter tube 312 of the PICC 310 including an integrated optical-fiber stylet 424 in accordance with some embodiments. FIG. 4B illustrates a longitudinal cross-section of the catheter tube 312 of the PICC 310 including the integrated optical-fiber stylet 424 in accordance with some embodiments.

As shown, the PICC 310 includes the catheter tube 312, a bifurcated hub 314, two extension legs 316, and two Luer connectors 318 operably connected in the foregoing order. The catheter tube 312 includes two catheter-tube lumens 413 and the optical-fiber stylet 424 disposed in a longitudinal bead 425 of the catheter tube 312 such as between the two catheter-tube lumens 413, as extruded. Optionally, in a same or different longitudinal bead of the catheter tube 312, the PICC 310 can further include an ECG stylet or ECG electrodes electrically connected by a cable to the ECG componentry in the console 140 or 240 for detecting the sequence of heartbeats. The bifurcated hub 314 has two hub lumens correspondingly fluidly connected to the two catheter-tube lumens 413. Each extension leg of the two extension legs 316 has an extension-leg lumen fluidly connected to a hub lumen of the two hub lumens. The PICC 310 further includes a stylet extension tube 320 extending from the bifurcated hub 314. The stylet extension tube 320 can be a skived portion of the catheter tube 312 including the optical-fiber stylet 424 or the skived portion of the catheter tube 312 disposed in another tube, either of which can terminate in a plug 322 for establishing an optical connection between the optical fiber 528 of the optical-fiber connector module 120 and the optical-fiber stylet 424 of the PICC 310.

The optical-fiber stylet 424 includes a number of FBG sensors 426a, 426b, 426c, . . . , 426n along at least a distal-end portion of the optical-fiber stylet 424 configured for shape sensing with the shape-sensing system 100 or 200. The FBG sensors 426a, 426b, 426c, . . . , 426n include periodic variations in refractive index of the optical fiber of the optical-fiber stylet 424, thereby forming wavelength-specific reflectors configured to reflect the input optical signals sent into the optical-fiber stylet 424 by the optical interrogator 130 or 230. FIG. 4B illustrates, in particular, a last three FBG sensors 426a, 426b, and 426c in the distal-end portion of the optical-fiber stylet 424, which FBG sensors 426*a*, 426*b*, and 426*c* are particularly useful in identifying a distinctive change or periodic changes in plotted curvature of the optical-fiber stylet 424 as set forth above. This is because the last three FBG sensors 426*a*, 426*b*, and 426*c* directly experience a physical change in curvature of the optical-fiber stylet 424 when, in this case, a tip of the PICC 310 is advanced into a heart of a patient by way of, for example, an SVC.

While the PICC 310 is provided as a particular embodiment of the medical device 110 of the shape-sensing system 100 or 200, it should be understood that any medical device of a number of medical devices including catheters such as a CVC can include at least an optical-fiber stylet and a stylet extension tube terminating in a plug for establishing an optical connection between the optical-fiber stylet of the medical device and the optical interrogator 130 or 230, optionally by way of the optical fiber 528 of the optical-fiber connector module 120.

Optical-Fiber Connector Modules

Figure 5:
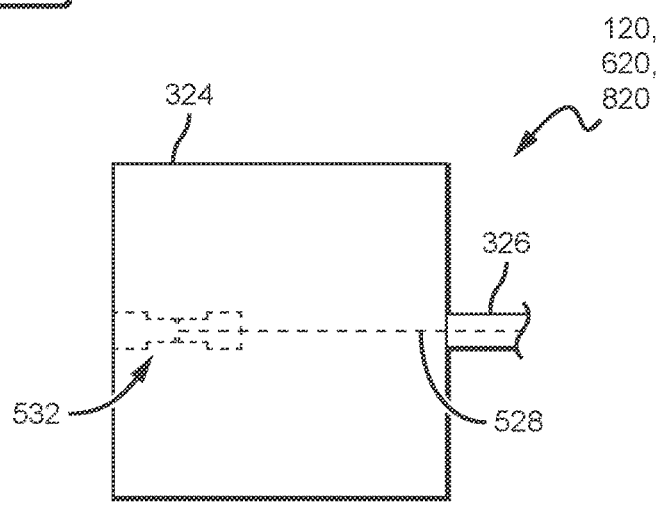
FIG. 5 illustrates a detailed section of an optical-fiber connector module in accordance with some embodiments.
Figure 6:
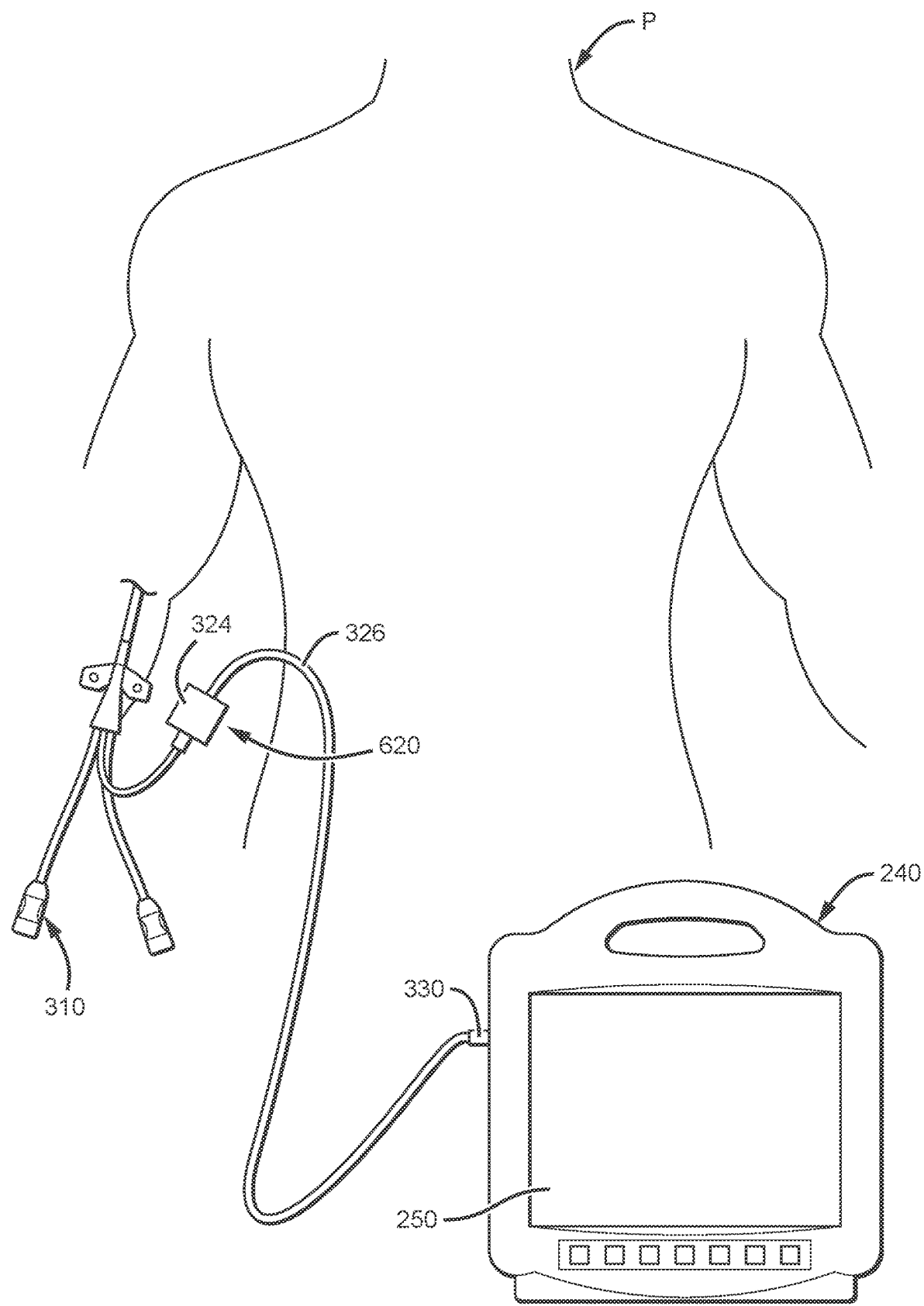
FIG. 6 illustrates the second shape-sensing system with a first optical-fiber connector module in accordance with some embodiments.
Figure 7:
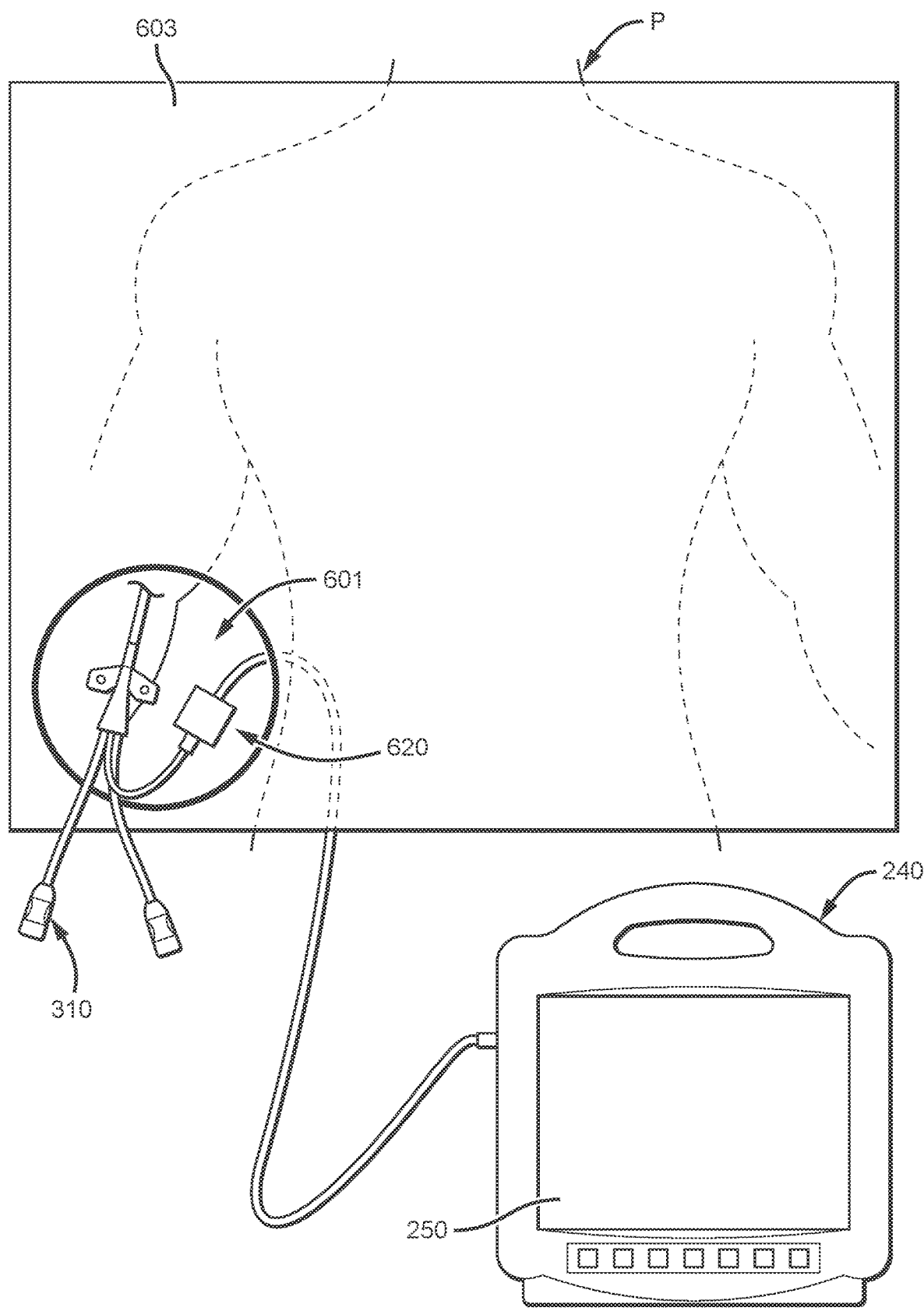
FIG. 7 illustrates the second shape-sensing system with the first optical-fiber connector module within a fenestration of a surgical drape in accordance with some embodiments.
Figure 8:
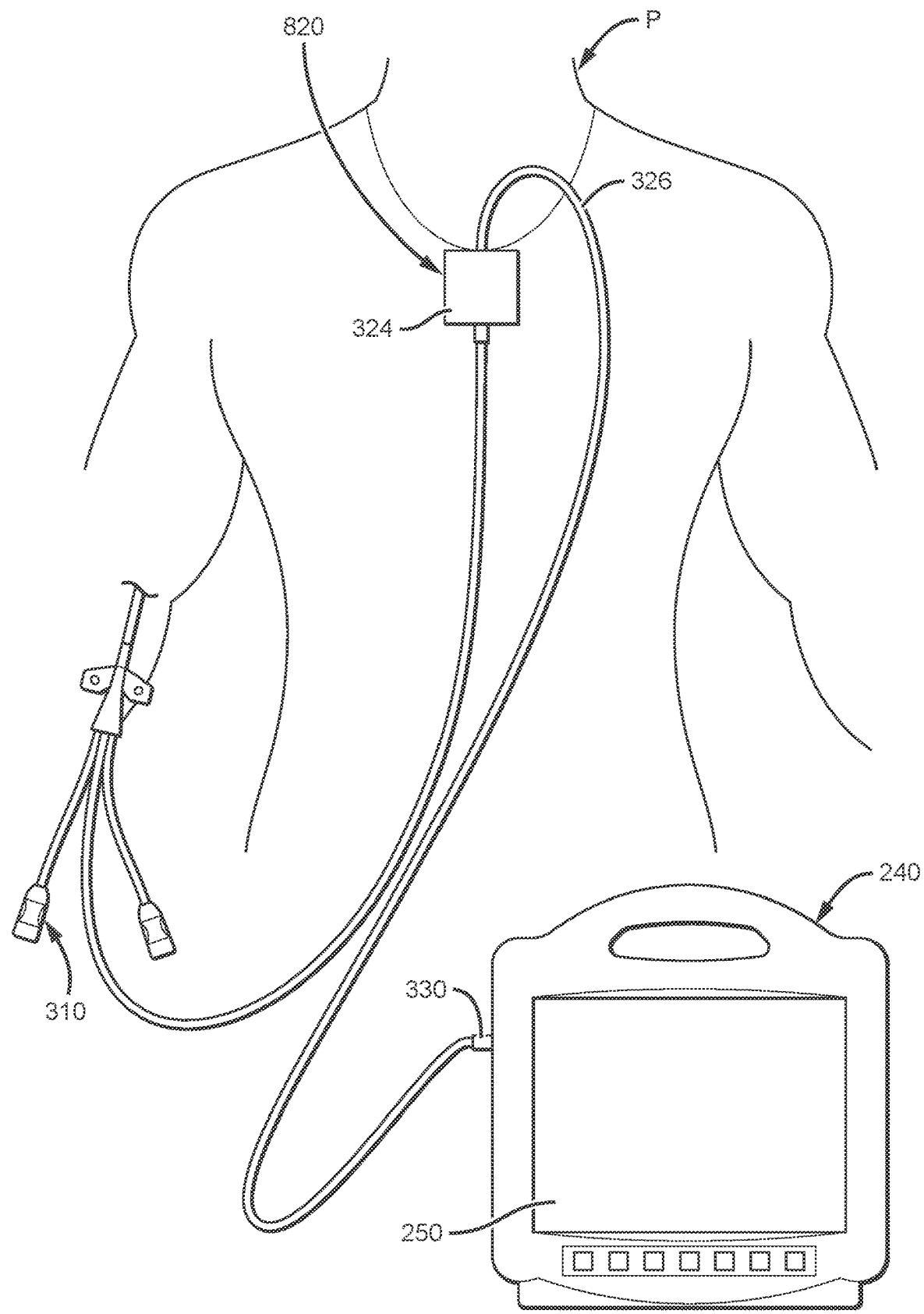
FIG. 8 illustrates the second shape-sensing system with a second optical-fiber connector module in accordance with some embodiments.
Figure 9:
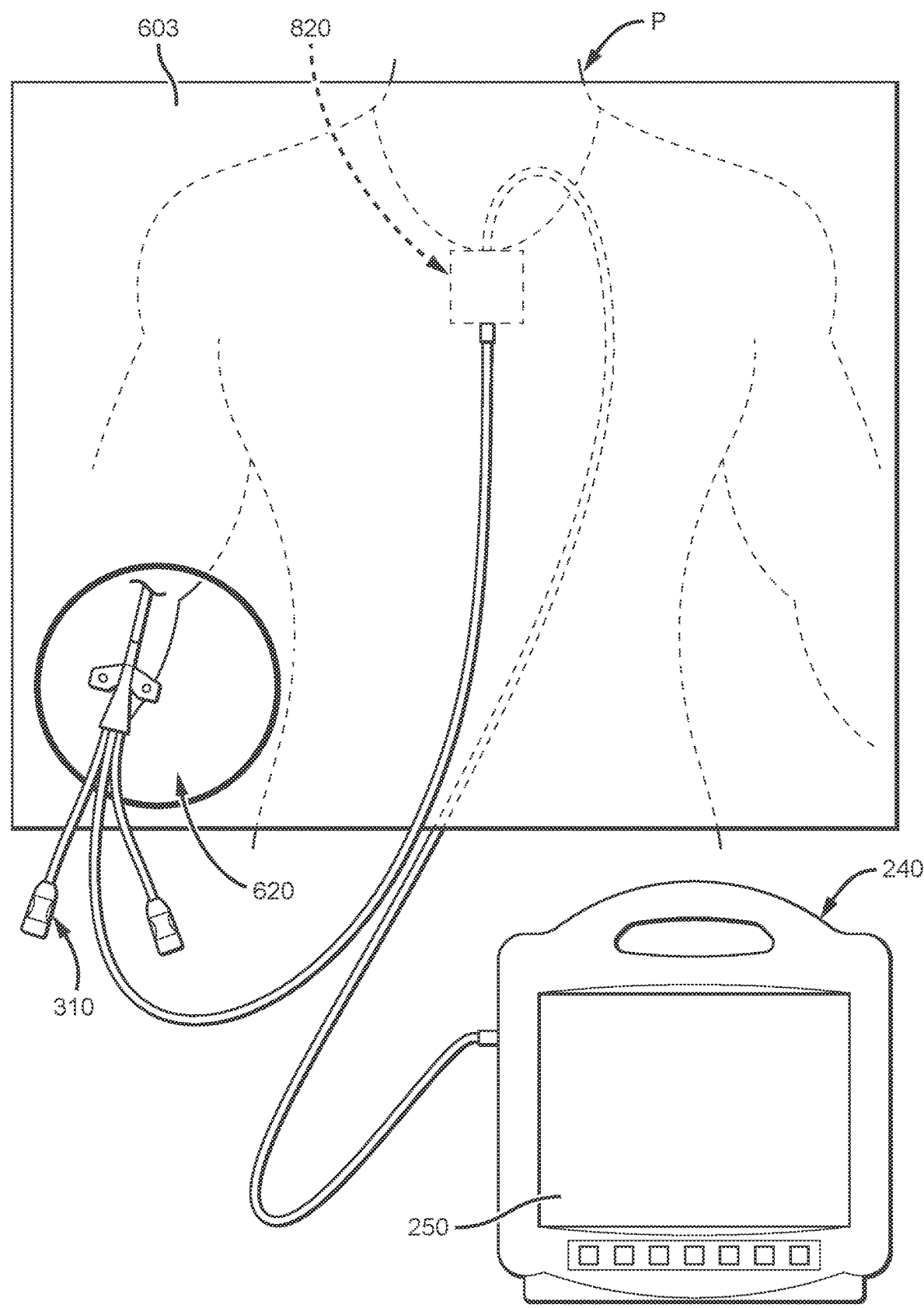
FIG. 9 illustrates the second shape-sensing system with the second optical-fiber connector module beneath a surgical drape in accordance with some embodiments.

FIG. 6 illustrates the second shape-sensing system 200 with a first optical-fiber connector module 620 in accordance with some embodiments. FIG. 7 illustrates the second shape-sensing system 200 with the first optical-fiber connector module 620 within a fenestration 601 of a surgical drape 603 in accordance with some embodiments. FIG. 8 illustrates the second shape-sensing system 200 with a second optical-fiber connector module 820 in accordance with some embodiments. FIG. 9 illustrates the second shape-sensing system 200 with the second optical-fiber connector module 820 beneath the surgical drape 603 in accordance with some embodiments. FIG. 5 illustrates a detailed section of the optical-fiber connector module 120 in accordance with some embodiments thereof such as the first optical-fiber connector module 620 or the second optical-fiber connector module 820.

As shown, the optical-fiber connector module 620 or 820 includes the housing 324, the receptacle 532 disposed in the housing 324, the cable 326 extending from the housing 324, and the optical fiber 528 within at least the cable 326.

The receptacle 532 includes an optical receiver configured to accept insertion of an optical terminal of a plug of the medical device 110 (e.g., the plug 322 of the PICC 310) for establishing an optical connection between the optical-fiber connector module 620 or 820 and the optical-fiber stylet of the medical device 110 (e.g., the optical-fiber stylet 424 of the PICC 310) when the plug is inserted into the receptacle 532.

The cable 326 includes the plug 330 for establishing an optical connection between the optical-fiber connector module 620 or 820 and the optical interrogator 230 of the console 240.

The optical fiber 528 extends from the receptacle 532 through the cable 326 to the plug 330. The optical fiber 528 is configured to convey the input optical signals from the optical interrogator 230 to the optical-fiber stylet of the medical device 110 (e.g., the optical-fiber stylet 424 of the PICC 310) and the reflected optical signals from the optical-fiber stylet to the optical interrogator 230.

As set forth above, the optical-fiber connector module 620 or 820 can further include the one-or-more sensors 222 selected from the gyroscope, the accelerometer, and the magnetometer disposed within the housing 324. The one-or-more sensors 222 are configured to provide sensor data for determining a reference plane for shape sensing with the optical-fiber stylet of the medical device 110 (e.g., the optical-fiber stylet 424 of the PICC 310).

While not shown, the optical-fiber connector module 620 or 820 can further include power and data wires extending from the one-or-more sensors 222 through the cable 326 to the plug 330 or another plug. The power and data wires are configured to respectively convey power to the one-or-more sensors 122 and data from the one-or-more sensors 122 to the console 240 when the one-or-more sensors 122 are present in the optical-fiber connector module 620 or 820.

The optical-fiber connection module 620 is configured to sit within the fenestration 601 of the surgical drape 603 adjacent a percutaneous insertion site for the medical device 110 (e.g., a catheter such as the PICC 310). As the optical-fiber connection module 620 is configured to sit within the fenestration 601 of the surgical drape 603, the optical-fiber connection module 620 is amenable to disinfection or sterilization. For example, the housing 324 of the optical-fiber connection module 620 can be a non-porous or chemically resistant to oxidants. The optical-fiber connection module 620 can be configured for manual disinfection with a ChloraPrep® product by Becton, Dickinson and Company (Franklin Lakes, N.J.), or the optical-fiber connection module 620 can be configured for automatic high-level disinfection or sterilization with vaporized $H_2O_2$ by way of Trophon® by Nanosonics Inc. (Indianapolis, Ind.).

In contrast to the optical-fiber connection module 620, the optical-fiber connection module 820 is configured to sit beneath the surgical drape 603 on a chest of a patient P. As such, the optical-fiber connection module 820 need not require a same level of disinfection or sterilization as the optical-fiber connection module 620.

While not shown, the housing 324 the optical-fiber connection module 820 includes a loop extending from the housing 324, a tether point integrated into the housing 324, a ball-lock-pin receiver integrated into the housing 324, or the like configured for attaching a neck strap to the optical-fiber connector module 820. The loop, the tether point, the ball-lock-pin receiver, or the like enables the optical-fiber connector module 820 to be secured to a neck of the patient P while sitting on the patient's chest. Additionally or alternatively, the housing 324 includes a patient-facing surface (e.g., a back of the optical-fiber connection module 820) configured to be adhered to the patient's chest. The patient-facing surface enables the optical-fiber connector module 820 to be secured to the patient's chest while sitting on the patient's chest whether or not the optical-fiber connection module 820 is also secured to the patient's neck.

Again, the receptacle 532 includes an optical receiver configured to accept insertion of an optical terminal of a plug of the medical device 110 (e.g., the plug 322 of the PICC 310) and form an optical connection when the plug is inserted into the receptacle 532; however, with the optical-fiber connector module 820, the optical connection is formed with the surgical drape 603 between the optical-fiber connector module 820 and the medical device 110. The receptacle 532 and the plug of the medical device 110 enable at least the optical connection from a sterile field (e.g., above the surgical drape 603) including the medical device 110 such as the PICC 310 to a non-sterile field (e.g., beneath the surgical drape 603) including the optical-fiber connection module 820 by way of breaching the surgical drape 603.

Methods

A method of the shape-sensing system 100 or 200 includes a shape-sensing step of shape sensing with the optical-fiber stylet (e.g., the optical-fiber stylet 424) of the shape-sensing system 100 or 200 while the tip of the medical device 110 or the optical-fiber stylet is advanced through a vasculature of a patient toward a heart.

The method further includes a detecting step of detecting a sequence of heartbeats with the heartbeat-detecting means of the shape-sensing system 100 or 200 for detecting the sequence of heartbeats while the tip of the medical device 110 of the optical-fiber stylet thereof is advanced through the vasculature of the patient toward the heart.

The method further includes a signal-sending step of sending the input optical signals into the optical-fiber stylet by the optical interrogator 130 or 230 and a signal-receiving step of receiving the FBG sensor-reflected optical signals from the optical-fiber stylet with the optical interrogator 130 or 230.

The method further includes a first converting step of converting the sequence of heartbeats into a heartbeat frequency by way of the heartbeat-converter algorithm of the console 140 or 240 of the shape-sensing system 100 or 200.

The method further includes a second converting step of converting the FBG sensor-reflected optical signals received from the optical-fiber stylet into plottable data by way of the number of optical signal-converter algorithms of the console 140 or 240.

The second converting step can include passing the FBG sensor-reflected optical signals, or the corresponding data, for the selection of the FBG sensors along the distal-end portion of the optical-fiber stylet through the band-pass filtering algorithm of the optical signal-converter algorithms. As set forth above, the band-pass filtering algorithm is configured to pass therethrough the FBG sensor-reflected optical signals, or the corresponding data, for the selection of the FBG sensors occurring with one or more frequencies within a range of frequencies around the heartbeat frequency while rejecting the FBG sensor-reflected optical signals, or the corresponding data, occurring with one or more frequencies outside the range of frequencies around the heartbeat frequency.

The second converting step can include passing the FBG sensor-reflected optical signals, or the corresponding data, for the FBG sensors proximal of the selection of the FBG sensors through the band-stop filtering algorithm of the optical signal-converter algorithms. The band-stop filtering algorithm is configured to reject the FBG sensor-reflected optical signals, or the corresponding data, occurring with one or more frequencies within the range of frequencies around the heartbeat frequency while passing therethrough the FBG sensor-reflected optical signals, or the corresponding data, occurring with one or more frequencies outside the range of frequencies around the heartbeat frequency.

The method further includes a plotting step of plotting a number of plots in view of filtering the FBG sensor-reflected optical signals, or the corresponding data, through the band-pass and band-stop filtering algorithms of the optical signal-converter algorithms. The number of plots can include a plot of curvature vs. time for each FBG sensor of the selection of the FBG sensors on the display screen 150 or 250 of the shape-sensing system 100 or 200. The number of plots can include a displayable shape over a 3-dimensional grid corresponding to the optical-fiber stylet in 3-dimensional space. The displayable shape is substantially free from heartbeat-related hydrodynamic noise.

The method further includes a displaying step of displaying on the display screen 150 or 250 the periodic changes in strain in the plot of curvature vs. time for any FBG sensor of the selection of the FBG sensors at a moment the tip of the medical device 110 or the optical-fiber stylet thereof is advanced into the heart of the patient.

Each method of a number of methods for determining whether the tip of the medical device 110 is located within a heart of a patient includes an advancing step of advancing the tip of the medical device 110 through a vasculature of the patient toward the heart. As set forth above, the medical device 110 (e.g., the PICC 310) includes the integrated optical-fiber stylet (e.g., the optical-fiber stylet 424) having the number of FBG sensors (e.g. the FBG sensors 426a, 426b, 426c, . . . , 426n) along at least the distal-end portion of the optical-fiber stylet for shape sensing with the shape-sensing system 100 or 200 including the medical device 110. When the medical device 110 is the PICC 310, the advancing step can include advancing the tip of the PICC 310 through a right basilic vein, a right axillary vein, a right subclavian vein, a right brachiocephalic vein, and into an SVC. When the medical device is a CVC, the advancing step includes advancing the tip of the CVC through a right internal jugular vein, a right brachiocephalic vein, and into the SVC.

The method can include enabling certain functions of the shape-sensing system 100 or 200 by turning on the console 140 or 240, running one or more programs on the console 140 or 240, making the selection of the FBG sensors (e.g., a selection of the FBG sensors 426a, 426b, 426c . . . , 426n) in the distal-end portion of the optical-fiber stylet for the plots of curvature vs. time 1012a, 1012b, 1012c, . . . , 1012n, making the optical or electrical connections, or the like as needed for various functions of the shape-sensing system 100 or 200.

Enabling certain functions of the shape-sensing system 100 or 200 can include a first enabling or allowing step of enabling or allowing the input optical signals to be sent into the optical-fiber stylet by the optical interrogator 130 or 230 of the shape-sensing system 100 or 200 while advancing the tip of the medical device 110 through the vasculature of the patient.

Enabling certain functions of the shape-sensing system 100 or 200 can include a second enabling or allowing step of enabling or allowing a sequence of heartbeats to be converted into a heartbeat frequency by way of the heartbeat-converter algorithm of the console 140 or 240 of the shape-sensing system 100 or 200. The second enabling or allowing step is during a detecting step of detecting the sequence of heartbeats with the heartbeat-detecting means of the shape-sensing system 100 or 200 for detecting the sequence of heartbeats while advancing the tip of the medical device 110 through the vasculature of the patient.

Enabling certain functions of the shape-sensing system 100 or 200 can include a third enabling or allowing step of enabling or allowing the FBG sensor-reflected optical signals to be received from the optical-fiber stylet by the optical interrogator 130 or 230 while advancing the tip of the medical device 110 through the vasculature of the patient.

Enabling certain functions of the shape-sensing system 100 or 200 can include a fourth enabling or allowing step of enabling or allowing the FBG sensor-reflected optical signals received from the optical-fiber stylet to be algorithmically converted into plottable data by way of the number of optical signal-converter algorithms.

The optical signal-converter algorithms can include the band-pass filtering algorithm for a selection of the FBG sensors (e.g., a last three FBG sensors) along the distal-end portion of the optical-fiber stylet. The band-pass filtering algorithm passes therethrough the FBG sensor-reflected optical signals, or the corresponding data, occurring with one or more frequencies within a range of frequencies around the heartbeat frequency while rejecting the FBG sensor-reflected optical signals or corresponding data occurring with one or more frequencies outside the range of frequencies around the heartbeat frequency.

The optical signal-converter algorithms can include the band-stop filtering algorithm for the FBG sensors proximal of the selection of the FBG sensors. The band-stop filtering algorithm rejects the FBG sensor-reflected optical signals, or the corresponding data, occurring with one or more frequencies within the range of frequencies around the heartbeat frequency while passing therethrough the FBG sensor-reflected optical signals, or the corresponding data, occurring with one or more frequencies outside the range of frequencies around the heartbeat frequency.

Enabling certain functions of the shape-sensing system 100 or 200 can include a fifth enabling or allowing step of enabling or allowing the plottable data to be plotted in a number of different plots (e.g., the plot of curvature vs. arc length 1004, the plot of torsion vs. arc length 1006, the plot of angle vs. arc length 1008, the plot of position vs. time 1010, one or more of the plots of curvature vs. time 1012a, 1012b, 1012c . . . , 1012n, etc.) on the display screen 150 or 250 of the shape-sensing system 100 or 200.

Enabling certain functions of the shape-sensing system 100 or 200 can include a sixth enabling or allowing step of enabling or allowing the FBG sensor-reflected optical signals received from the optical-fiber stylet to be algorithmically converted into the displayable shapes over the 3-dimensional grid 1002 for the medical device 110 on the display screen 150 or 250 of the shape-sensing system 100 or 200.

The method can include an identifying step of manually identifying on the display screen 150 or 250 the distinctive change in the plotted curvature of the optical-fiber stylet sensed by the selection of the FBG sensors in the distal-end portion of the optical-fiber stylet at the moment the tip of the medical device 110 is advanced into the heart, thereby determining the tip of the medical device 110 is located within the heart. The identifying step can include identifying the instantaneous increase in the plotted curvature of the optical-fiber stylet followed by the instantaneous decrease in the plotted curvature as sensed by each FBG sensor of the last three FBG sensors (e.g., the FBG sensors 426a, 426b, and 426c) in the distal-end portion of the optical-fiber stylet at the moment the tip of the medical device 110 is advanced into the heart. Additionally or alternatively, the method can include a determining step of automatically determining with the heart-determiner algorithm the distinctive change in the plotted curvature of the optical-fiber stylet, or the plottable data therefor, sensed by the selection of the FBG sensors in the distal-end portion of the optical-fiber stylet at the moment the tip of the medical device 110 is advanced into the heart.

The method can include a ceasing step of ceasing to advance the tip of the medical device 110 through the vasculature of the patient after determining the tip of the medical device 110 is located in the heart.

The method can include an identifying or confirming step of identifying or confirming the tip of the medical device 110 is in the heart by way of periodic changes in the plotted curvature of the optical-fiber stylet sensed by the selection of the FBG sensors. For example, the identifying step can include identifying on the display screen 150 or 250 the periodic changes in strain in the plot of curvature vs. time for any FBG sensor of the selection of the FBG sensors at a moment the tip of the medical device 110 is advanced into the heart of the patient, thereby determining the tip of the medical device 110 is located within the heart.

Notably, not one method of the shape-sensing system 100 or 200 requires an X-ray for determining whether the tip of the medical device 110 is located within the heart of the patient. As such, patients need not be exposed to ionizing X-ray radiation when the shape-sensing system 100 or 200 is used. In addition, not one method of the shape-sensing system 100 or 200 requires an additional magnetic-sensor piece of capital equipment for determining whether the tip of the medical device 110 is located within the heart of the patient. In addition, since, the shape-sensing system 100 or 200 does not require use of a reliable ECG P-wave like some existing systems for placing a tip of a medical device into a heart of a patient, the shape-sensing system 100 or 200 can be used with patient having atrial fibrillation or another heart arrhythmia.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A shape-sensing system, comprising:
one or more medical devices including:
an integrated optical-fiber stylet having a plurality of fiber Bragg grating ("FBG") sensors along a distal-end portion of the integrated optical-fiber stylet; and
a heartbeat-detecting means for detecting a sequence of heartbeats;
a console including memory and one or more processors configured to:
convert the sequence of heartbeats into a heartbeat frequency by way of a heartbeat-converter algorithm; and
convert FBG sensor-reflected optical signals from the integrated optical-fiber stylet into plottable data by way of a plurality of optical signal-converter algorithms, the optical signal-converter algorithms including a band-pass filtering algorithm for a selection of the FBG sensors along the distal-end portion of the integrated optical-fiber stylet, the band-pass filtering algorithm configured to pass therethrough the FBG sensor-reflected optical signals or corresponding data occurring with one or more frequencies within a range of frequencies around the heartbeat frequency while rejecting the FBG sensor-reflected optical signals or corresponding data occurring with one or more frequencies outside the range of frequencies around the heartbeat frequency; and
a display screen configured for displaying any plot of a plurality of plots of the plottable data, the plurality of plots including a plot of curvature vs. time for each FBG sensor of the selection of the FBG sensors for identifying periodic changes in strain of the integrated optical-fiber stylet at a moment a tip of the integrated optical-fiber stylet is advanced into a heart of a patient.

2. The shape-sensing system of claim 1, wherein the plurality of optical signal-converter algorithms include a band-stop filtering algorithm for the FBG sensors proximal of the selection of the FBG sensors, the band-stop filtering algorithm configured to reject the FBG sensor-reflected optical signals or corresponding data occurring with one or more frequencies within the range of frequencies around the heartbeat frequency while passing therethrough the FBG sensor-reflected optical signals or corresponding data occurring with one or more frequencies outside the range of frequencies around the heartbeat frequency.

3. The shape-sensing system of claim 2, wherein the plurality of plots of the plottable data include a displayable shape over a 3-dimensional grid corresponding to the integrated optical-fiber stylet in 3-dimensional space, the displayable shape substantially free from heartbeat-related hydrodynamic noise.

4. The shape-sensing system of claim 1, wherein the heartbeat-detecting means is incorporated into a same medical device as that including the integrated optical-fiber stylet.

5. The shape-sensing system of claim 4, wherein the same medical device including the integrated optical-fiber stylet has electrocardiogram ("ECG") electrodes electrically connected by a cable to ECG componentry in the console for detecting the sequence of heartbeats.

6. The shape-sensing system of claim 4, wherein same medical device including the integrated optical-fiber stylet has one or more lumens configured to contain a saline solution, the same medical device including a cable to connect the one or more lumens when filled with the saline solution to electrocardiogram ("ECG") componentry in the console for detecting the sequence of heartbeats.

7. The shape-sensing system of claim 1, wherein the heartbeat-detecting means is incorporated into a different medical device than that including the integrated optical-fiber stylet.

8. The shape-sensing system of claim 7, wherein the different medical device includes electrocardiogram ("ECG") skin electrodes electrically connected to ECG componentry in the console for detecting the sequence of heartbeats.

9. The shape-sensing system of claim 1, the console including an heart-determiner algorithm configured to automatically confirm on the display screen the tip of the integrated optical-fiber stylet is in the heart of the patient by way of the periodic changes in the strain of the integrated optical-fiber stylet sensed by the selection of the FBG sensors, the periodic changes in the strain resulting from heartbeat-related hydrodynamics.

10. The shape-sensing system of claim 1, further comprising an optical interrogator configured to send input optical signals into the integrated optical-fiber stylet and receive the FBG sensor-reflected optical signals from the integrated optical-fiber stylet, the optical interrogator being either a stand-alone optical interrogator or an integrated optical interrogator integrated into the console.

11. A method of a shape-sensing system, comprising:
shape sensing with an optical-fiber stylet of the shape-sensing system while a tip of the optical-fiber stylet is advanced through a vasculature of a patient toward a heart, the optical-fiber stylet having a plurality of fiber Bragg grating ("FBG") sensors along a distal-end portion of the optical-fiber stylet for the shape sensing;
detecting a sequence of heartbeats with a heartbeat-detecting means of the shape-sensing system for detecting the sequence of heartbeats while the tip of the optical-fiber stylet is advanced through the vasculature of the patient toward the heart;
converting the sequence of heartbeats into a heartbeat frequency by way of a heartbeat-converter algorithm of a console of the shape-sensing system;
converting FBG sensor-reflected optical signals received from the optical-fiber stylet into plottable data by way of a plurality of optical signal-converter algorithms of the console, the converting including passing the FBG sensor-reflected optical signals or corresponding data for a selection of the FBG sensors along a distal-end portion of the optical-fiber stylet through a band-pass filtering algorithm of the plurality of optical signal-converter algorithms, the band-pass filtering algorithm configured to pass therethrough the FBG sensor-reflected optical signals or corresponding data for the selection of the FBG sensors occurring with one or more frequencies within a range of frequencies around the heartbeat frequency while rejecting the FBG sensor-reflected optical signals or corresponding data occurring with one or more frequencies outside the range of frequencies around the heartbeat frequency;
plotting a plurality of plots including a plot of curvature vs. time for each FBG sensor of the selection of the FBG sensors on a display screen of the shape-sensing system; and
displaying on the display screen periodic changes in strain in the plot of curvature vs. time for any FBG sensor of the selection of the FBG sensors at a moment the tip of the optical-fiber stylet is advanced into the heart of the patient.

12. The method of claim 11, wherein the converting step includes passing the FBG sensor-reflected optical signals or corresponding data for the FBG sensors proximal of the selection of the FBG sensors through a band-stop filtering algorithm of the plurality of optical signal-converter algorithms, the band-stop filtering algorithm configured to reject the FBG sensor-reflected optical signals or corresponding data occurring with one or more frequencies within the range of frequencies around the heartbeat frequency while passing therethrough the FBG sensor-reflected optical signals or corresponding data occurring with one or more frequencies outside the range of frequencies around the heartbeat frequency.

13. The method of claim 11, wherein the plurality of plots includes a displayable shape over a 3-dimensional grid corresponding to the optical-fiber stylet in 3-dimensional space, the displayable shape substantially free from heartbeat-related hydrodynamic noise.

14. The method of claim 11, wherein the heartbeat-detecting means includes electrocardiogram ("ECG") electrodes of a medical device including the optical-fiber stylet, ECG skin electrodes, or a combination thereof connected to ECG componentry in the console for detecting the sequence of heartbeats.

15. The method of claim 11, further comprising sending input optical signals into the optical-fiber stylet by an optical interrogator and receiving the FBG sensor-reflected optical signals from the optical-fiber stylet with the optical interrogator, the optical interrogator being either a stand-alone optical interrogator or an integrated optical interrogator integrated into the console.

16. A method for determining a tip of a medical device is located within a heart, comprising:
advancing the tip of the medical device through a vasculature of a patient toward the heart, the medical device including an integrated optical-fiber stylet having a plurality of fiber Bragg grating ("FBG") sensors along a distal-end portion of the integrated optical-fiber stylet for shape sensing with a shape-sensing system including the medical device;

detecting a sequence of heartbeats with a heartbeat-detecting means of the shape-sensing system for detecting the sequence of heartbeats while advancing the tip of the medical device through the vasculature of the patient toward the heart;

allowing the sequence of heartbeats to be converted into a heartbeat frequency by way of a heartbeat-converter algorithm of a console of the shape-sensing system;

allowing FBG sensor-reflected optical signals received from the integrated optical-fiber stylet while advancing the tip of the medical device through the vasculature of the patient to be converted into plottable data by way of a plurality of optical signal-converter algorithms of the console, the optical signal-converter algorithms including a band-pass filtering algorithm for a selection of the FBG sensors along a distal-end portion of the optical-fiber stylet, the band-pass filtering algorithm configured to pass therethrough the FBG sensor-reflected optical signals or corresponding data occurring with one or more frequencies within a range of frequencies around the heartbeat frequency while rejecting the FBG sensor-reflected optical signals or corresponding data occurring with one or more frequencies outside the range of frequencies around the heartbeat frequency;

allowing a plurality of plots including a plot of curvature vs. time for each FBG sensor of the selection of the FBG sensors to be plotted on a display screen of the shape-sensing system; and identifying on the display screen periodic changes in strain in the plot of curvature vs. time for any FBG sensor of the selection of the FBG sensors at a moment the tip of the medical device is advanced into the heart of the patient, thereby determining where the tip of the medical device is located within the heart.

17. The method of claim 16, wherein the plurality of optical signal-converter algorithms include a band-stop filtering algorithm for the FBG sensors proximal of the selection of the FBG sensors, the band-stop filtering algorithm configured to reject the FBG sensor-reflected optical signals or corresponding data occurring with one or more frequencies within the range of frequencies around the heartbeat frequency while passing therethrough the FBG sensor-reflected optical signals or corresponding data occurring with one or more frequencies outside the range of frequencies around the heartbeat frequency.

18. The method of claim 17, wherein the plurality of plots includes a displayable shape over a 3-dimensional grid corresponding to the integrated optical-fiber stylet in 3-dimensional space, the displayable shape substantially free from heartbeat-related hydrodynamic noise.

19. The method of claim 16, wherein the heartbeat-detecting means includes electrocardiogram ("ECG") electrodes of the medical device, ECG skin electrodes, or a combination thereof connected to ECG componentry in the console for detecting the sequence of heartbeats.

20. The method of claim 16, wherein the step of advancing the tip of the medical device through the vasculature of the patient includes advancing the tip of the medical device through a right internal jugular vein, a right brachiocephalic vein, and into a superior vena cava ("SVC").

21. The method of claim 20, wherein the integrated optical-fiber stylet is disposed in a central venous catheter ("CVC").

22. The method of claim 16, wherein the step of advancing the tip of the medical device through the vasculature of the patient includes advancing the tip of the medical device through a right basilic vein, a right axillary vein, a right subclavian vein, a right brachiocephalic vein, and into a superior vena cava ("SVC").

23. The method of claim 22, wherein the medical device is a peripherally inserted central catheter ("PICC").

24. The method of claim 16, further comprising ceasing to advance the tip of the medical device through the vasculature of the patient after determining the tip of the medical device is located in the heart.

* * * * *